US009921341B2

(12) United States Patent
Laredo et al.

(10) Patent No.: US 9,921,341 B2
(45) Date of Patent: Mar. 20, 2018

(54) LOW-WATER CONTENT ACRYLATE-ACRYLAMIDE COPOLYMERS FOR OPHTHALMIC DEVICES

(71) Applicant: Novartis AG, Basel (CH)

(72) Inventors: Walter Laredo, Fort Worth, TX (US); Ali E. Akinay, Southlake, TX (US); Xuwei Jiang, Arlington, TX (US); David Jinkerson, Benbrook, TX (US); Vincent Nguyen, Grapevine, TX (US); Douglas Schlueter, Azle, TX (US)

(73) Assignee: Novartis AG, Basel (CH)

( * ) Notice: Subject to any disclaimer, the term of this patent is extended or adjusted under 35 U.S.C. 154(b) by 73 days.

(21) Appl. No.: 14/967,760

(22) Filed: Dec. 14, 2015

(65) Prior Publication Data

US 2016/0170093 A1    Jun. 16, 2016

Related U.S. Application Data

(60) Provisional application No. 62/092,325, filed on Dec. 16, 2014.

(51) Int. Cl.
| | |
|---|---|
| *G02B 1/04* | (2006.01) |
| *A61L 27/52* | (2006.01) |
| *A61L 27/26* | (2006.01) |
| *A61L 27/50* | (2006.01) |

(52) U.S. Cl.
CPC .............. *G02B 1/043* (2013.01); *A61L 27/26* (2013.01); *A61L 27/50* (2013.01); *A61L 27/52* (2013.01); *G02B 1/041* (2013.01); *A61L 2430/16* (2013.01)

(58) Field of Classification Search
None
See application file for complete search history.

(56) References Cited

U.S. PATENT DOCUMENTS

| | | | |
|---|---|---|---|
| 3,162,676 A | 12/1964 | Goldberg et al. | |
| 3,299,173 A | 1/1967 | Roselli | |
| 4,304,895 A | 12/1981 | Loshaek | |
| 4,436,887 A * | 3/1984 | Chromecek | A61L 27/16 351/159.33 |
| 4,528,311 A | 7/1985 | Beard et al. | |
| 4,612,358 A | 9/1986 | Besecke et al. | |
| 4,716,234 A | 12/1987 | Dunks et al. | |
| 4,834,750 A | 5/1989 | Gupta | |
| 5,290,892 A | 3/1994 | Namdaran et al. | |
| 5,331,073 A | 7/1994 | Weinschenk, III et al. | |
| 5,470,932 A | 11/1995 | Jinkerson | |
| 5,603,774 A | 2/1997 | LeBoeuf et al. | |
| 5,693,095 A | 12/1997 | Freeman et al. | |
| 5,922,821 A | 7/1999 | LeBoeuf et al. | |
| 6,140,438 A | 10/2000 | Ojio et al. | |
| 6,241,766 B1 | 6/2001 | Liao et al. | |
| 6,245,106 B1 | 6/2001 | Makker et al. | |
| 6,313,187 B2 | 11/2001 | LeBoeuf et al. | |
| 6,329,485 B1 | 12/2001 | Vanderbilt | |
| 6,353,069 B1 | 3/2002 | Freeman et al. | |
| 6,528,602 B1 | 3/2003 | Freeman et al. | |
| 6,653,422 B2 | 11/2003 | Freeman et al. | |
| 6,657,032 B2 | 12/2003 | Vanderbilt | |
| 6,703,466 B1 | 3/2004 | Karakelle et al. | |
| 6,780,899 B2 | 8/2004 | Liao et al. | |
| 6,806,337 B2 | 10/2004 | Schlueter et al. | |
| 6,852,793 B2 | 2/2005 | Salamone et al. | |
| 6,872,793 B1 | 3/2005 | Schlueter | |
| 7,585,900 B2 | 9/2009 | Cordova et al. | |
| 7,605,190 B2 | 10/2009 | Moszner et al. | |
| 7,652,076 B2 | 1/2010 | Schlueter et al. | |
| 7,714,039 B2 | 5/2010 | Cordova et al. | |
| 7,790,824 B2 | 9/2010 | Freeman | |
| 7,790,825 B2 | 9/2010 | Lehman et al. | |
| 7,799,845 B2 | 9/2010 | Schlueter | |
| 7,847,046 B2 | 12/2010 | Schlueter et al. | |
| 8,048,154 B2 | 11/2011 | Schlueter | |
| 8,058,323 B2 | 11/2011 | Cordova et al. | |
| 8,153,703 B2 | 4/2012 | Laredo | |
| 8,207,244 B2 | 6/2012 | Laredo | |
| 8,232,326 B2 | 7/2012 | Laredo | |
| 8,329,097 B1 * | 12/2012 | Kunzler | B29D 11/00125 264/2.6 |
| 8,362,177 B1 | 1/2013 | Lehman et al. | |
| 8,449,610 B2 | 5/2013 | Laredo et al. | |
| 8,466,209 B2 | 6/2013 | Akinay et al. | |
| 8,557,892 B2 | 10/2013 | Laredo | |
| 2005/0063996 A1 * | 3/2005 | Peyman | A61K 9/0048 424/400 |
| 2006/0134169 A1 | 6/2006 | Linhardt et al. | |
| 2006/0275342 A1 | 12/2006 | Lindhardt et al. | |
| 2007/0010883 A1 | 1/2007 | Mentak | |
| 2008/0081851 A1 | 4/2008 | Benz et al. | |
| 2008/0269370 A1 * | 10/2008 | Myung | A61L 27/38 523/105 |
| 2009/0232871 A1 | 9/2009 | Hitz et al. | |
| 2012/0202916 A1 | 8/2012 | Laredo et al. | |
| 2014/0178595 A1 | 6/2014 | Bothe et al. | |

OTHER PUBLICATIONS

International Searching Authority, International Search Report and Written Opinion, PCT/US2015/065508, dated Mar. 3, 2016, 13 pages.

* cited by examiner

*Primary Examiner* — Tae H Yoon

(74) *Attorney, Agent, or Firm* — Jian Zhou

(57) ABSTRACT

Acrylate-acrylamide copolymers are disclosed. They are rigid and glassy in dry state at room temperature (from about 23° C. to about 28° C.), but are soft and very deformable and have a high refractive index, a high glistening resistance and a low aging-related surface light scattering in fully hydrated state. They are particularly suitable for making wet-packed intraocular lenses (IOLs) which can be delivered through sub 2.0 mm incisions.

20 Claims, No Drawings

LOW-WATER CONTENT ACRYLATE-ACRYLAMIDE COPOLYMERS FOR OPHTHALMIC DEVICES

This application claims the benefit under 35 U.S.C. § 119(e) of U.S. provisional application Ser. No. 62/092,325 filed on Dec. 16, 2014, herein incorporated by reference in its entirety.

This invention is directed to ophthalmic device materials. In particular, this invention relates to acrylate-acrylamide copolymers which, in a hydrated stated, are soft, highly deformable and essentially free of glistenings and have a high refractive index materials and with other desirable properties, which are especially suitable for making wet-packed intraocular lenses (IOLs) which can be delivered through sub 2.0 mm incisions.

BACKGROUND OF THE INVENTION

With advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Conventional silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than conventional silicone materials.

Acrylic materials suitable for intraocular lenses are generally soft and hydrophobic and have an equilibrium water content of less than 5% by weight. See, for example, those described in U.S. Pat. Nos. 4,834,750, 5,290,892, 5,331,073, 5,693,095, 5,922,821, 6,241,766, 6,245,106, 6,313,187, 6,353,069, 6,528,602, 6,653,422, 6,703,466, 6,780,899, 6,806,337, 6,872,793, 7,585,900, 7,652,076, 7,714,039, 7,790,824, 7,790,825, 7,799,845, 7,847,046, 8,058,323, 8,362,177, 8,466,209, 8,449,610, 8,557,892 (herein incorporated by references in their entireties). However, soft hydrophobic acrylic materials can be tacky. It is generally desirable to reduce the amount of surface tack in materials intended for use as a foldable intraocular lens. Tacky materials can be difficult to manufacture, handle, and unfold. Attempts have been made to reduce tackiness so that the lenses are easier to process or handle, easier to fold or deform, and have shorter unfolding times. For example, U.S. Pat. No. 5,603,774 discloses a plasma treatment process for reducing the tackiness of a soft acrylic material. U.S. Pat. Nos. 6,241,766; 6,245,106; 7,585,900; 7,714,039 and 8,362,177 disclose use of hydrophilic components or additives for reducing the tackiness of a soft acrylic material.

In addition, a soft hydrophobic acrylic material is susceptible to have glistenings (or microvacuoles) which are formed in vivo and can affect adversely the optical performance of intraocular lenses. Glistenings are tiny inclusions of water present within the matrix of an IOL material and are visible due to differences in refractive indices between the IOL material and water within the IOL material. It is reported that a polyethylene glycol (PEG)-containing polymerizable component (monomer and/or crosslinker) (U.S. Pat. Nos. 5,693,095, 6,353,069, and 8,449,610) can be used to improve glistening resistance of hydrophobic acrylic formulations. But, in order to minimize its adverse effects on the refractive index of acrylic materials, low amounts of PEG dimethacrylate or PEG mono-(meth)acrylate concentrations are often required. Addition of PEG dimethacrylates or PEG mono-(meth)acrylates also tends to decrease the modulus and tensile strength of the resulting copolymer.

U.S. Pat. No. 6,140,438 discloses the use of a hydrophilic monomer for improving glistening resistance of soft hydrophobic acrylic materials and the use of an alkyl (meth)acrylate for improving the flexibility and the shape restoration property of soft hydrophobic acrylic materials.

U.S. Pat. Nos. 6,329,485 and 6,657,032 disclose soft, foldable hydrogel lens materials which have a water content of approximately 5 to 30 percent by weight and are made from a composition comprising two principal monomers, one aromatic high refractive index monomer and one hydrophilic (meth)acrylate monomer (e.g., hydroxyethyl methacrylate) in an amount greater than that of the aromatic high refractive index monomer.

U.S. Pat. No. 6,852,793 discloses polymeric compositions which have a water content from 4.5 to 15 percent by weight, a relatively high refractive index of approximately 1.45 or greater, and a relatively high elongation of approximately 80 percent or greater and which are produced through the polymerization of one or more copolymers with one or more hydrophilic monomers (preferably N,N-dimethylacrylamide) and optionally one or more aromatic-based monomers, hydrophobic monomers or a combination thereof.

SUMMARY OF THE INVENTION

The present invention provides acrylate/acrylamide copolymer materials which are particularly suited for use as wet-packed intraocular lenses (IOLs).

The present invention is partly based on the finding that acrylamide acrylate monomers can be copolymerized to obtain acrylate/acrylamide copolymer materials which are rigid and glassy in dry state at room temperature, but upon hydration can have an elongation at break (maximum strain) of greater than 90%, a Young's modulus of about 45 MPa or less, a 100% secant modulus of less than 5.0 MPa, a refractive index of greater than 1.50, an equilibrium water content (EWC) of from about 5% to about 11% by weight, and a high resistance against glistenings (no bright field glistenings and minimal dark field glistenings) induced by temperature changes. Because of their rigid and glassy forms in dry state at room temperature, intraocular lenses cast molded in molds from a material of the invention can be easily demolded and handled. Such a relatively high value of elongation at break and a low 100% secant modulus value indicate that the subject materials are soft and highly deformable. With high glistening resistance, high refractive index and high softness and deformability, the subject materials are suitable for microincision applications. The present invention is also partly based on the discovery that, by selection and combination of acrylamide monomers, acrylate monomers, acrylamide crosslinker, acrylate crosslinker, and hydrophilic monomer(s), and/or in combination with improved processing (inert casting and degassing molds), the subject material can have minimized age-related degradation (as characterized by low surface light scattering of less than 30 CCT units (computer-compatible-tape units) after 10-years accelerated aging (90° C., 81 days in a Balanced Salt Solution, BSS, from Alcon)). The present invention is further partly based on the discovery that, by combining use of a polyethyleneglycol-based hydrophilic agent, the latent haze occurred when heating from the room temperature to 35° C. can be substantially reduced or eliminated. In this application, the term "minimal or no latent haze" or "latent haze issue being substantially reduced or eliminated" means that a hydrated material remains substantially clear (i.e., $$\frac{T_{23} - T_{35}}{T_{23}} \leq 20\%,$$

in which $T_{23}$ and $T_{35}$ are average transmittances between 400 nm to 700 nm of the material at 23° C. and 35° C. respectively) when being heated from 23° C. to 35° C. It is believed that an acrylate/acrylamide copolymeric material with a relatively high concentration of acrylamide monomer can have a relatively-low critical solution temperature (LOST). When such a material in hydrated state is heated from room temperature to a temperature (e.g., 35° C.) above the LOST, phase separation can occur, causing the material become hazy and lose clarity (namely "latent haze"). This latent haze issue can hinder the use of acrylate/acrylamide copolymers as a wet-packed IOL material. By minimizing or eliminating this latent haze issue, the subject materials are suitable for making wet-packed, glistening resistant, higher refractive index IOLs for microincision applications.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

Unless indicated otherwise, all component amounts are presented on a % (w/w) basis ("wt. %").

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), C$_1$-C$_4$ alkyl, C$_1$-C$_4$ alkoxy, C$_1$-C$_4$ alkylthio (alkyl sulfide), C$_1$-C$_4$ acylamino, C$_1$-C$_4$ alkylamino, di-C$_1$-C$_4$ alkylamino, halogen atom (Br or Cl), and combinations thereof.

In general, the invention is directed to ophthalmic device materials which are rigid and glassy in dry state at room temperature (from about 23° C. to about 28° C.), but which are soft and very deformable and have a high refractive index, a high glistening resistance and a low aging-related surface light scattering in fully hydrated state.

An ophthalmic device material of the invention is a polymerization product of a polymerizable composition selected from the group consisting of composition A1, composition A2 and composition A3, wherein composition A1 comprises (a1) from about 18% to about 32% (preferably from about 20% to about 30%, more preferably from about 22.5% to 27.5%) by weight of N,N-dimethylacrylamide, (b1) at least one hydrophobic acrylamido component selected from the group consisting of N-butyl acrylamide, N-butoxymethyl acrylamide, N-methoxypropyl acrylamide, and N,N'-hexamethylene bisacrylamide (preferably from the group consisting of N-butyl acrylamide, N-butoxymethylacrylamide and N,N'-hexamethylene bisacrylamide), (c1) from about 40% to about 76% by weight (preferably from about 45% to about 74% by weight, more preferably from about 50% to about 72% by weight) of said one or more aryl acrylic monomers of formula (I)

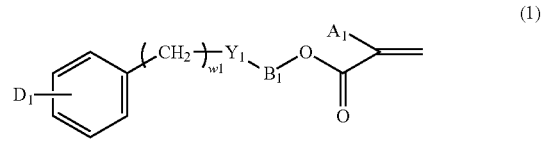

wherein A$_1$ is H or CH$_3$ (preferably H); B$_1$ is (CH$_2$)$_{m1}$ or [O(CH$_2$)$_2$]$_{z1}$ in which m1 is 2-6 and z1 is 1-10; Y$_1$ is a direct bond, O, S, or NR' in which R' is H, CH$_3$, C$_{n'}$H$_{2n'+1}$ in which n'=1-10, iso-OC$_3$H$_7$, C$_6$H$_5$, or CH$_2$C$_6$H$_5$; W1 is 0-6, provided that m1+w1≤8; and D$_1$ is H, Cl, Br, C$_1$-C$_4$ alkyl, C$_1$-C$_4$ alkoxy, C$_6$H$_5$, or CH$_2$C$_6$H$_5$, wherein composition A2 comprises (a2) from about 15% to about 35% (preferably from about 20% to about 30%, more preferably from about 22.5% to 27.5%) by weight of N-methylacrylamide, (b2) at least one polymerizable crosslinking agent, (c2) from about 60% to about 80% by weight of one or more aryl acrylic monomers of formula (I) as defined above, wherein composition A3 comprises (a3) from about 10% to about 35% (preferably from about 15% to about 30%) by weight of a mixture of N,N-dimethylacrylamide and N-hydroxyethylacrylamide, (b3) at least one polymerizable crosslinking agent, (c3) from about 60% to about 80% by weight of one or more aryl acrylic monomers of formula (I) as defined above, wherein the ophthalmic device material in a dry state has a glass transition temperature of greater than 23° C. (preferably greater than 25° C., more preferably from about 28° C. to about 40° C.), wherein the ophthalmic device material in a fully-hydrated state has: a refractive index of greater than 1.50 (preferably 1.51, more preferably 1.52) measured at 589 nm and at room temperature (23±3° C.), an equilibrium water content of from about 5% to 11% (preferably from about 6% to about 10%, more preferably from about 7% to about 9%) by weight at a temperature of from 16° C. to 45° C., a glistening resistance characterized by having no bright field microvacuoles and about 10 or less microvacuoles per viewing screen in glistering tests, a Young's modulus of from about 1.0 MPa to about 45.0 MPa (preferably from about 2.5 MPa to about 40 MPa, more preferably from about 5.0 MPa to 35.0 MPa), a 100% secant modulus of less than 5.0 MPa (preferably about 3.0 MPa or less, more preferably about 1.5 MPa or less). Preferably, it has an elongation at break of greater than 90% (preferably at least about 100%, more preferably at least about 110%), and/or a surface light scattering of about 30 CCT or less after 10-years accelerated aging (90° C., 81 days in a Balanced Salt Solution, BSS, from Alcon).

In accordance with the invention, a device material of the invention should have a glass transition temperature (Tg) greater than 23° C. (preferably greater than 25° C., more preferably from about 28° C. to about 40° C.) in dry state, but have a glass transition temperature of less than 20° C. (preferably less than 15° C., more preferably less than 10° C.) in a fully hydrated state.

For use in IOLs, the device materials in a fully-hydrated state of the present invention preferably exhibit sufficient strength, low stiffness, and low 100% secant modulus to allow devices made of them to be soft and highly deformable for microincision applications. Thus, an ophthalmic device material of the present invention will have: an elongation (% strain at break) of greater than 150% (preferably at least about 180%, more preferably between about 200% and about 400%); a Young's modulus of from about 1.0 MPa to about 45.0 MPa (preferably from about 2.5 MPa to about 40 MPa, more preferably from about 5.0 MPa to 35.0 MPa); and a 100% secant modulus of less than 5.0 MPa, preferably about 3.0 MPa or less, more preferably about 1.5 MPa or less). With such properties lenses made of such a material generally will not crack, tear or split when folded. Elongation of polymer samples is determined on dumbbell shaped tension test specimens with a 20 mm total length, length in the grip area of 11 mm, overall width of 2.49 mm, 0.833 mm width of the narrow section, a fillet radius of 8.83 mm, and a thickness of 0.9 mm. Testing is performed on samples at ambient conditions (23±2° C., 50±5% relative humidity) using an Instron Material Tester (Model No. 4442 or equivalent) with a 50 Newton load cell. The grip distance is set at 11 mm and a crosshead speed is set at 50 mm/minute and the sample is pulled until failure. The elongation (strain) is reported as a fraction of the displacement at failure to the original grip distance. The strain at break is reported as a fraction of the displacement at failure to the original grip distance. Stress at break is calculated at the maximum load for the sample, typically the load when the sample breaks, assuming that the initial area remains constant. The Young's modulus is calculated from the instantaneous slope of the stress-strain curve in the linear elastic region. The 50% secant modulus is calculated as the slope of a straight line drawn on the stress-strain curve between 0% strain and 50% strain. The 100% secant modulus is calculated as the slope of a straight line drawn on the stress-strain curve between 0% strain and 100% strain. Since materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test is begun.

A device material of the present invention preferably further has an equilibrium water content of from about 5% to 11% (preferably from about 6% to about 10%, more preferably from about 7% to about 9%) by weight across the temperature range of 16-45° C. The device materials are preferably resistant to glistenings such that when equilibrated in water at 45° C. and subsequently allowed to cool to ambient temperature (approximately 22° C.) should produce no BF microvacuoles and at most 10 DF microvacuoles as detected by microscopic examination.

Aryl acrylic monomers of formula (I) can be made by methods known in the art. For example, the conjugate alcohol of the desired monomer can be combined in a reaction vessel with methyl acrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding acrylic acid to the conjugate alcohol and catalyzing with a carbodiimide or mixing the conjugate alcohol with acryloyl chloride and a base such as pyridine or triethylamine.

Suitable aryl acrylic monomers of formula (I) include, but are not limited to: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methyl benzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl)ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl) ethyl acrylate; 2-(4-cyclohexylphenyl)ethyl methacrylate; 2-(2-chlorophenyl)ethyl acrylate; 2-(2-chlorophenyl)ethylmethacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.

Preferred aryl acrylic monomers of formula (I) are those wherein $B_1$ is $(CH_2)_{m1}$ is 2-5, $Y_1$ is nothing or O, w1 is 0 or 1, and $D_1$ is H. Most preferred are 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; 2-[2-(benzyloxy)ethoxy]ethyl acrylate; and their corresponding methacrylates.

The polymerizable composition for making an ophthalmic device material of the invention comprises one or more hydrophobic acrylamide component selected from the group consisting of N-butyl acrylamide, N-butoxymethyl acrylamide, N-methoxypropyl acrylamide, and N,N'-hexamethylene bisacrylamide (preferably from the group consisting of N-butyl acrylamide, N-butoxymethylacrylamide and N,N'-hexamethylene bisacrylamide). It is believed that a hydrophobic acrylamide component may be added to reduce surface light scattering after 10 years of accelerating aging in a balanced salt solution (at 90° C. for 81 days).

The polymerizable composition for making an ophthalmic device material of the invention further comprises from about 5% to about 15% by weight of 2-hydroxyethyl methacrylate. It is believed that 2-hydroxyethyl methacrylate may also be added to reduce surface light scattering after 10 years of accelerating aging in a balanced salt solution (at 90° C. for 81 days).

The polymerizable composition for making an ophthalmic device material of the invention further comprises a poly(ethylene glycol)-containing (PEG-containing) polymerizable component. It is believed that a PEG-containing polymerizable component may also be added to reduce or eliminate latent haze issue occurred when heating a material in a fully-hydrated state of the invention from 23° C. to 35° C., namely the material in the fully hydrated state remains substantially clear (i.e., $$\frac{T_{23} - T_{35}}{T_{23}} \leq 20\%,$$

in which $T_{23}$ and $T_{35}$ are average transmittances between 400 nm to 700 nm of the material at 23° C. and 35° C. respectively) when being heated from 23° C. to 35° C.).

In accordance with the invention, a PEG-containing polymerizable component can be a linear poly(ethylene glycol) with one or two terminal polymerizable groups as described above, or a branched poly(ethylene glycol) with three or more terminal polymerizable groups as described above. Such a PEG-containing polymerizable component can be prepared according to methods known in the art from commercially available polyethylene glycols with one or more terminal functional groups (e.g., hydroxyl, amino, or carboxyl groups). Generally, a poly(ethylene glycol) with one or more hydroxyl terminal groups is dissolved in tetrahydrofuran and treated with a (meth)acrylic acid derivative such as methacryloyl chloride or methacrylic anhydride in the presence of triethylamine or pyridine. The reaction proceeds until greater than 90% of the hydroxyl groups have been converted to the corresponding acrylic or methacrylic esters. The polymer solution is filtered and the polymer is isolated by precipitation into diethyl ether. Amine and carboxylic acid terminated polyethylene glycols are functionalized in a similar manner using suitable (meth)acrylic acid derivatives.

Preferably, a PEG-containing polymerizable component used in the invention is represented by formula (II)

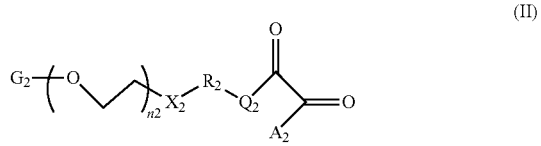

(II)

wherein: $A_2$ is H or $CH_3$; $Q_2$ and $Q_2'$ independent of each other are a direct bond, O, NH, or $C(=O)NHCH_2CH_2O$; $X_2$ and $X_2'$ independent of each other are a direct bond, O, NH, $OC(=O)NH$, or $NHC(=O)NH$ (preferably a direct bond or O); $R_2$ and $R_2'$ independent of each other are a direct bond, or $(CH_2)_p$ (preferably a direct bond); p=1-3; $G_2$ is H, $C_1$-$C_4$ alkyl, $(CH_2)_{m2}NH_2$, $(CH_2)_{m2}CO_2H$, or $R_2'$—$X_2'$-$Q_2'$-$C(=O)CA_2=CH_2$ (preferably $C_1$-$C_4$ alkyl or $R_2'$—$X_2'$-$Q_2'$-$C(=O)CA_2=CH_2$); m2=2-6; and n2=45-225 when G=H, $C_1$-$C_4$ alkyl, $(CH_2)_{m2}NH_2$, or $(CH_2)_{m2}CO_2H$; otherwise, n2=51-225 (preferably n2=45-180 when $G_2$=$C_1$-$C_4$ alkyl, otherwise, n2=51-225).

PEG-containing polymerizable components of formula (II) can be made by methods known in the art. For example, they can be prepared according to the procedures described above or as described in U.S. Pat. No. 8,449,610 (herein incorporated by reference in its entirety).

Although the total amount of the PEG-containing polymerizable component of formula (II) contained in the device materials of the present invention is from about 1% to about 5% by weight (preferably from about 2% to about 5% by weight, more preferably from about 2% to about 4% by weight), of the total amount of polymerizable components of the device materials, such amount may comprise one PEG-containing polymerizable component of formula (II) or combinations of PEG-containing polymerizable components of formula (II). The PEG-containing polymerizable component of formula (II) has a number average molecular weight of 2,000-10,000 Daltons, preferably 2,000-8,000 Daltons, more preferably 2,000-6,000 Daltons, and most preferably 2,500-6,000 Daltons.

The polymerizable composition for making an ophthalmic device material of the invention preferably further comprises a polymerizable cross-linking agent. The cross-linking agent may be any terminally ethylenically unsaturated compound having more than one unsaturated groups. Suitable cross-linking agents include, for example: ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; ethylene glycol diacrylate; diethylene glycol diacrylate; triethylene glycol diacrylate, tetraethylene glycol diacrylate, allyl acrylate; 1,3-propanediol diacrylate; 2,3-propanediol diacrylate; 1,6-hexanediol diacrylate; 1,4-butanediol diacrylate; N,N'-hexamethylene bisacrylamide; N,N'-hexamethylene bismethacrylamide; N,N'-dihydroxyethylene bisacrylamide; N,N'-dihydroxyethylene bismethacrylamide; N,N'-methylene bisacrylamide; N,N'-methylene bismethacrylamide; $CH_2=C(CH_3)C(=O)O—(CH_2CH_2O)_p—C(=O)C(CH_3)=CH_2$ where p=1-50; $CH_2=CHC(=O)O—(CH_2CH_2O)_p—C(=O)CH=CH_2$ where p=1-50; $CH_2=C(CH_3)C(=O)O(CH_2)_tO—C(=O)C(CH_3)=CH_2$ where t=3-20; and $CH_2=CHC(=O)O(CH_2)_tO—C(=O)CH=CH_2$ where t=3-20. A preferred cross-linking monomer is 1,6-hexanediol diacrylate, 1,4-butanediol diacrylate, or N,N'-hexamethylene bisacrylamide.

Generally, the total amount of the cross-linking component is from about 0.4% to about 2.5% by weight, more preferably from about 0.8% to about 1.5% by weight.

In addition to one or more monomers of formula (I), one or more hydrophobic acrylamide components, one or more PEG-containing polymerizable components of formula (II), and one or more cross-linking agents, the polymerizable composition for making an ophthalmic device material may also contain other ingredients, including, but not limited to, polymerizable UV-absorbers (or UV-absorbing agents), polymerizable colored dyes, siloxane monomers, and combinations thereof.

A polymerizable ultraviolet (UV) absorbing agent can also be included in the materials of the present invention. The polymerizable UV-absorbing agent can be any compound which absorbs UV light (i.e., light having a wavelength shorter than about 380 nm) and optionally high-energy-violet-light (HEVL) (i.e., light having a wavelength between 380 nm and 440 nm), but does not absorb any substantial amount of visible light having a wavelength greater than 440 nm. The UV-absorbing compound is incorporated into the monomer mixture and is entrapped in the polymer matrix when the monomer mixture is polymerized. Any suitable polymerizable UV-absorbing agents can be used in the invention. A polymerizable UV-absorbing agent used in the invention comprises a benzophenone-moiety or preferably a benzotriazole-moiety. Polymerizable benzophenone-containing UV-absorbing agents can be prepared according to procedures described in U.S. Pat. Nos. 3,162,676 and 4,304,895 (herein incorporated by reference in their entirety) or can be obtained from commercial suppliers. Polymerizable benzotriazole-containing UV-absorbing agents can be prepared according to procedures described in U.S. Pat. Nos. 3,299,173, 4,612,358, 4,716,234, 4,528,311, 8,153,703, and U.S. Pat. No. 8,232,326 (herein incorporated by reference in their entireties) or can be obtained from commercial suppliers.

Examples of preferred polymerizable benzophenone-containing UV-absorbing agents include without limitation 2-hydroxy-4-acryloxy alkoxy benzophenone, 2-hydroxy-4-methacryloxy alkoxy benzophenone, allyl-2-hydroxybenzophenone, 4-acryloylethoxy-2-hydroxybenzophenone (UV2), 2-hydroxy-4-methacryloyloxybenzophenone (UV7), or combinations thereof.

Examples of preferred polymerizable benzotriazole-containing UV-absorbing and UV/HEVL-absorbing agents include without limitation: 2-(2-hydroxy-5-vinylphenyl)-2H-benzotriazole, 2-(2-hydroxy-5-acryyloxyphenyl)-2H-benzotriazole, 2-(2-hydroxy-3-methacrylamido methyl-5-tert octylphenyl) benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5-methacryloxypropylphenyl) benzotriazole, 2-hydroxy-5-methoxy-3-(5-(trifluoromethyl)-2H-benzo[d][1,2,3]triazol-2-yl)benzyl methacrylate (WL-1), 2-hydroxy-5-methoxy-3-(5-methoxy-2H-benzo[d][1,2,3]triazol-2-yl)benzyl methacrylate (WL-5), 3-(5-fluoro-2H-benzo[d][1,2,3]triazol-2-yl)-2-hydroxy-5-methoxybenzyl methacrylate (WL-2), 3-(2H-benzo[d][1,2,3]triazol-2-yl)-2-hydroxy-5-methoxybenzyl methacrylate (WL-3), 3-(5-chloro-2H-benzo[d][1,2,3]triazol-2-yl)-2-hydroxy-5-methoxybenzyl methacrylate (WL-4), 2-hydroxy-5-methoxy-3-(5-methyl-2H-benzo[d][1,2,3]triazol-2-yl)benzyl methacrylate (WL-6), 2-hydroxy-5-methyl-3-(5-(trifluoromethyl)-2H-benzo[d][1,2,3]triazol-2-yl)benzyl methacrylate (WL-7), 4-allyl-2-(5-chloro-2H-benzo[d][1,2,3]triazol-2-yl)-6-methoxyphenol (WL-8), 2-{2'-Hydroxy-3'-tert-5'[3"-(4"-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl-(UVAM), 2-(2'-hydroxy-5'-methacryloxyethylphenyl) benzotriazole (2-Propenoic acid, 2-methyl-, 2-[3-(2H-benzotriazol-2-yl)-4-hydroxyphenyl] ethyl ester, Norbloc), 2-{2'-Hydroxy-3'-tert-butyl-5'-[3'-methacryloyloxypropoxy]phenyl}-5-methoxy-2H-benzotriazole (UV13), 242'-Hydroxy-3'-tert-butyl-5'-[3'-acryloyloxypropoxy)phenyl]-5-trifluoromethyl-2H-benzotriazole (CF₃-UV13), 2-(2'-hydroxy-5-methacrylamidophenyl)-5-methoxybenzotriazole (UV6), 2-(3-allyl-2-hydroxy-5-methylphenyl)-2H-benzotriazole (UV9), 2-(2-Hydroxy-3-methallyl-5-methylphenyl)-2H-benzotriazole (UV12), 2-3'-t-butyl-2'-hydroxy-5'-(3"-dimethylvinylsilylpropoxy)-2'-hydroxyphenyl)-5-methoxybenzotriazole (UV15), 2-(2'-hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-Methylacrylic acid 3-[3-tert-butyl-5-(5-chlorobenzotriazol-2-yl)-4-hydroxyphenyl]-propyl ester (16-100, CAS#96478-15-8), 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (9Cl) (CAS#83063-87-0).

More preferably, a polymerizable UV-absorbing agent is 2-(2H-benzo[d][1,2,3]triazol-2-yl)-4-methyl-6-(2-methylallyl)phenol (oMTP), 3-[3-tert-butyl-4-hydroxy-5-(5-methoxy-2-benz[d][1,2,3]triazol-2-yl)phenoxy]propyl methacrylate (UV13), and 2-[3-(2H-benzotriazol-2-yl)-4-hydroxyphenyl]ethyl methacrylate (Norbloc 7966), or combinations thereof.

In addition to ultraviolet absorbing materials, ophthalmic devices made of the copolymers of the present invention may include colored dyes, such as the yellow dyes disclosed in U.S. Pat. Nos. 5,470,932 and 8,207,244.

The copolymers of this invention are prepared by conventional polymerization methods. For example, a mixture of N,N-dmethylacrylamide, one or more monomers of formula (I) and (III), and a cross-linking agent in the desired proportions, together with any other polymerizable components, such as a UV absorber, yellow dye, and a conventional free-radical initiator, e.g., a thermal initiator (or a photoinitiator), is prepared. The mixture can then be introduced into a mold of desired shape, and the polymerization carried out thermally (i.e., by heating) or photochemically (i.e., by actinic radiation, e.g., UV radiation and/or visible radiation) to activate the initiator.

Examples of suitable thermal initiators include: but are not limited to, azonitriles, such as 2,2'-azobis (2,4-dimethylpentanenitrile), 2,2'-azobis (2-methylpropanenitrile), 2,2'-azobis (2-methylbutanenitrile), 2,2'-azobis(isobutyronitrile) (AIBN); peroxides, such as benzoyl peroxide; peroxycarbonates, such as bis-(4-t-butylcyclohexyl) peroxydicarbonate (Perkadox 16), and the like. A preferred initiator is AIBN.

Where the polymerization is carried out photochemically, a mold should be transparent to actinic radiation of a wavelength capable of initiating polymerization. Conventional photoinitiator compounds, e.g., a benzophenone-type or bisacylphosphine oxide (BAPO) photoinitiator, can also be introduced to facilitate the polymerization. Suitable photoinitiators are benzoin methyl ether, diethoxyacetophenone, a benzoylphosphine oxide, 1-hydroxycyclohexyl phenyl ketone, Darocur and Irgacur types photoinitiators (preferably Darocur 1173®, Darocur 2959® and Irgacure 819®), and Germanium-based Norrish Type I photoinitiators which are capable of initiating a free-radical polymerization under irradiation with a light source including a light in the region of about 400 to about 550 nm. Examples of benzoylphosphine initiators include 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Examples of Germanium-based Norrish Type I photoinitiators are acylgermanium compounds described in U.S. Pat. No. 7,605,190 (herein incorporated by reference in its entirety).

Regardless of the chosen initiator or curing method, the curing process should be controlled to produce optically clear materials with no defects, low tack, and low pre-release from the mold interface as the material shrinks during polymerization.

Once the ophthalmic device materials of the present invention have been cured, they are extracted in a suitable solvent to remove as much of the unreacted components of the materials as possible. Examples of suitable solvents include acetone, methanol, and cyclohexane. A preferred solvent for extraction is acetone.

IOLs constructed of the disclosed ophthalmic device materials can be of any design capable of being rolled or folded into a small cross section that can fit through a relatively smaller incision. For example, the IOLs can be of what is known as a one piece or multipiece design. Typically, an IOL comprises an optic and at least one haptic. The optic is that portion which serves as the lens and the haptics are attached to the optic and are like arms which hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the ophthalmic device materials of the present invention are also suitable for use in other devices, including contact lenses, keratoprostheses, intracorneal lenses, corneal inlays or rings, and glaucoma filtration devices.

These device materials can be used to form intraocular lenses with low surface tack and high refractive indexes. Lenses made of these materials are flexible and transparent, can be inserted into the eye through a relatively small incision, and recover their original shape after having been inserted.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A polymeric ophthalmic device material, having: (1) a glass transition temperature of greater than 23° C. (preferably greater than 25° C., more preferably from about 28° C. to about 40° C.) in a dry state; (2) a glass transition temperature of about 20° C. or lower (preferably about 18° C. or lower, more preferably about 15° C. or lower) in a fully hydrated state; (3) a refractive index of greater than 1.50 (preferably greater than 1.51, more preferably greater than 1.52) measured at 589 nm and at room temperature (23±3° C.) in the fully hydrated state; (4) an equilibrium water content of from about 5% to 11% (preferably from about 6% to about 10%, more preferably from about 7% to about 9%) by weight at a temperature of from 16° C. to 45° C.; (5) a glistening resistance characterized by having no bright field microvacuole and about 10 or less microvacuoles per viewing screen in glistening tests; (5) a Young's modulus of from about 1.0 MPa to about 45.0 MPa (preferably from about 2.5 MPa to about 40 MPa, more preferably from about 5.0 MPa to 35.0 MPa); and (6) a 100% secant modulus of less than 5.0 MPa (preferably about 3.0 MPa or less, more preferably about 1.5 MPa or less), wherein the ophthalmic device material is a polymerization product of a polymerizable composition selected from the group consisting of composition A1, composition A2, and composition A3, wherein composition A1 comprises (a1) from about 18% to about 32% (preferably from about 20% to about 30%, more preferably from about 22.5% to 27.5%) by weight of N,N-dimethylacrylamide, (b1) at least one hydrophobic acrylamido component selected from the group consisting of N-butyl acrylamide, N-butoxymethyl acrylamide, N-methoxypropyl acrylamide, and N,N'-hexamethylene bisacrylamide (preferably from the group consisting of N-butyl acrylamide, N-butoxymethylacrylamide and N,N'-hexamethylene bisacrylamide), (c1) from about 40% to about 76% by weight (preferably from about 45% to about 74% by weight, more preferably from about 50% to about 72% by weight) of said one or more aryl acrylic monomers of formula (I)

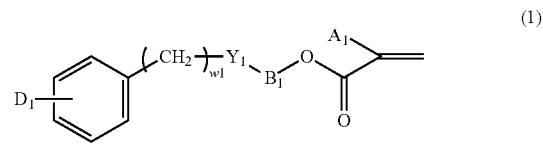

(1)

wherein $A_1$ is H or $CH_3$ (preferably H); $B_1$ is $(CH_2)_{m1}$ or $[O(CH_2)_2]_{z1}$ in which m1 is 2-6 and z1 is 1-10; $Y_1$ is a direct bond, O, S, or NR' in which R' is H, $CH_3$, $C_{n'}H_{2n'+1}$ in which n'=1-10, iso-$OC_3H_7$, $C_6H_5$, or $CH_2C_6H_5$; W1 is 0-6, provided that m1+w1≤8; and $D_1$ is H, Cl, Br, $C_1$-$C_4$ alkyl, $C_1$-$C_4$ alkoxy, $C_6H_5$, or $CH_2C_6H_5$, wherein composition A2 comprises (a2) from about 15% to about 35% (preferably from about 20% to about 30%, more preferably from about 22.5% to 27.5%) by weight of N-methylacrylamide, (b2) at least one polymerizable crosslinking agent, (c2) from about 60% to about 80% by weight of one or more aryl acrylic monomers of formula (I) as defined above, wherein composition A3 comprises (a3) from about 10% to about 35% (preferably from about 15% to about 30%) by weight of a mixture of N,N-dimethylacrylamide and N-hydroxyethylacrylamide, (b3) at least one polymerizable crosslinking agent, (c3) from about 60% to about 80% by weight of one or more aryl acrylic monomers of formula (I) as defined above.

2. The ophthalmic device material according to invention 1, wherein the ophthalmic device material in a dry state has a glass transition temperature of greater than 25° C., more preferably from about 28° C. to about 40° C.

3. The ophthalmic device material according to invention 1 or 2, wherein the ophthalmic device material in a dry state in a fully-hydrated state has: a glass transition temperature of about 18° C. or lower, more preferably about 15° C. or lower.

4. The ophthalmic device material according to any one of inventions 1 to 3, wherein the ophthalmic device material in a fully-hydrated state has a refractive index of greater than 1.51 (more preferably greater than 1.52) measured at 589 nm and at room temperature (23±3° C.)

5. The ophthalmic device material according to any one of inventions 1 to 4, wherein the ophthalmic device material in a fully-hydrated state has an equilibrium water content of from about 6% to about 10% (more preferably from about 7% to about 9%) by weight at a temperature of from 16° C. to 45° C.

6. The ophthalmic device material according to any one of inventions 1 to 5, wherein the ophthalmic device material in a fully-hydrated state has a Young's modulus of from about 2.5 MPa to about 40 MPa (more preferably from about 5.0 MPa to 35.0 MPa).

7. The ophthalmic device material according to any one of inventions 1 to 6, wherein the ophthalmic device material in a fully-hydrated state has a 100% secant modulus of about 3.0 MPa or less (more preferably about 1.5 MPa or less).

8. The ophthalmic device material according to any one of inventions 1 to 7, wherein the device material in the fully hydrated state has a surface light scattering of about 30 CCT or less after 10-years accelerated aging (90° C., 81 days in a balanced salt solution).

9. The ophthalmic device material according to any one of inventions 1 to 8, wherein the device material in the fully hydrated state remains substantially clear (i.e., $$\frac{T_{23} - T_{35}}{T_{23}} \le 20\%,$$

in which $T_{23}$ and $T_{35}$ are average transmittances between 400 nm to 700 nm of the material at 23° C. and 35° C. respectively) when being heated from 23° C. to 35° C.

10. The ophthalmic device material according to any one of inventions 1 to 9, wherein the device material in the fully hydrated state has an elongation at break of greater than 90%, preferably at least about 100%, more preferably at least about 110%.

11. The ophthalmic device material according to any one of inventions 1 to 10, wherein in formula (I), $B_1$ is $(CH_2)_{m1}$, m1 is 2-5, $Y_1$ is nothing or O, w1 is 0 or 1, and $D_1$ is H.

12. The ophthalmic device material according to any one of inventions 1 to 11, wherein said one or more aryl acrylic monomers of formula (I) are: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl) ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl) ethyl acrylate; 2-(4-cyclohexylphenyl)ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.

13. The ophthalmic device material according to any one of inventions 1 to 12, wherein said one or more aryl acrylic monomers of formula (I) are: 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; or combinations thereof.

14. The ophthalmic device material according to any one of inventions 1 to 13, wherein the polymerizable composition is composition A1.

15. The ophthalmic device material according to invention 14, wherein composition A1 comprises from about 18% to about 32% (preferably from about 20% to about 30%, more preferably from about 22.5% to 27.5%) by weight of N,N dimethylacrylamide.

16. The ophthalmic device material according to invention 14 or 15, wherein composition A1 comprises from about 40% to about 76% by weight (preferably from about 45% to about 74% by weight, more preferably from about 50% to about 72% by weight) of said one or more aryl acrylic monomers.

17. The ophthalmic device material according to any one of inventions 1 to 13, wherein the polymerizable composition is composition A2.

18. The ophthalmic device material according to invention 17, wherein composition A2 comprises from about 15% to about 35% (preferably from about 20% to about 30%, more preferably from about 22.5% to 27.5%) by weight of N-methylacrylamide.

19. The ophthalmic device material according to any one of inventions 1 to 13, wherein the polymerizable composition is composition A3.

20. The ophthalmic device material according to invention 19, wherein composition A3 comprises from about 10% to about 35% (preferably from about 15% to about 30%) by weight of a mixture of N,N-dimethylacrylamide and N-hydroxyethylacrylamide.

21. The ophthalmic device material according to any one of inventions 1 to 20, wherein the polymerizable composition further comprises at least one component selected from the group consisting of:
  (i) from about 5% to about 15% by weight of hydroxyethyl methacrylate;
  (ii) from about 1% to about 5% by weight of a poly(ethylene glycol)-containing polymerizable component of formula (II)

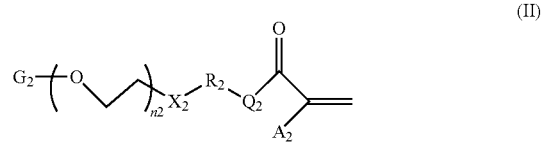

wherein: $A_2$ is H or $CH_3$; $Q_2$ and $Q_2'$ independent of each other are a direct bond, O, NH, or C(=O)

NHCH$_2$CH$_2$O; X$_2$ and X$_2$' independent of each other are a direct bond, O, NH, OC(=O)NH, or NHC(=O)NH (preferably a direct bond or O); R$_2$ and R$_2$' independent of each other are a direct bond, or (CH$_2$)$_p$ (preferably a direct bond); p=1-3; G$_2$ is H, C$_1$-C$_4$ alkyl, (CH$_2$)$_{m2}$NH$_2$, (CH$_2$)$_{m2}$CO$_2$H, or R$_2$'—X$_2$'-Q$_2$'-C(=O)CA$_2$=CH$_2$ (preferably C$_1$-C$_4$ alkyl or R$_2$'—X$_2$'-Q$_2$'-C(=O)CA$_2$=CH$_2$); m2=2-6; and n2=45-225 when G=H, C$_1$-C$_4$ alkyl, (CH$_2$)$_{m2}$NH$_2$, or (CH$_2$)$_{m2}$CO$_2$H; otherwise, n2=51-225 (preferably n2=45-180 when G$_2$=C$_1$-C$_4$ alkyl, otherwise, n2=51-225);

(iii) from about 0.4% to about 2.5% by weight by weight of a polymerizable crosslinking agent selected from the group consisting of ethylene glycol dimethacrylate, diethylene glycol dimethacrylate, triethylene glycol dimethacrylate, tetraethylene glycol dimethacrylate, allyl methacrylate, 1,3-propanediol dimethacrylate, 2,3-propanediol dimethacrylate, 1,6-hexanediol dimethacrylate, 1,4-butanediol dimethacrylate, ethylene glycol diacrylate, diethylene glycol diacrylate, triethylene glycol diacrylate, tetraethylene glycol diacrylate, allyl acrylate, 1,3-propanediol diacrylate, 2,3-propanediol diacrylate, 1,6-hexanediol diacrylate, 1,4-butanediol diacrylate, N,N'-hexamethylene bismethacrylamide, N,N'-dihydroxyethylene bisacrylamide, N,N'-dihydroxyethylene bismethacrylamide, N,N'-methylene bisacrylamide, and N,N'-methylene bismethacrylamide;

(iv) a polymerizable UV-absorbing agent; and (v) a combination thereof.

22. The ophthalmic device material according to invention 21, wherein the polymerizable composition comprises from about 2% to about 5% by weight (more preferably from about 2% to about 4% by weight) of a poly(ethylene glycol)-containing polymerizable component of formula (II).

23. The ophthalmic device material according to invention 21 or 22, wherein the PEG-containing polymerizable component of formula (II) has a number average molecular weight of 2,000-10,000 Daltons, preferably 2,000-8,000 Daltons, more preferably 2,000-6,000 Daltons, and most preferably 2,500-6,000 Daltons.

24. The ophthalmic device material according to any one of inventions 1 to 23, wherein the polymerizable composition comprises comprise a polymerizable crosslinking agent selected from the group consisting of 1,6-hexanediol diacrylate, 1,4-butanediol diacrylate, and a combination thereof.

25. An intraocular lens comprising an ophthalmic device material according to any one of inventions 1 to 24.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

Determination of Extractables

Testing for extractables was performed by weighing slabs before and after extraction (n=4) and drying to calculate extractables.

Equilibrium Water Content

Following % extractables determination, the same samples were placed into glass vials, immersed in a Balanced Salt Solution (BSS, Alcon) and placed into a 45° C. water bath for at least 24 hours, then removed and re-weighed to determine % equilibrium water content (EWC). In a few cases the water content was determined by weighing samples before and after MV testing.

Glistening Testing

For temperature-change-induced (ΔT-induced) microvacuole testing (glistening testing), samples were immersed in a Balanced Salt Solution (BSS, Alcon) in a glass vial and placed into a 45° C. water bath for at least 24 hours, then removed and cooled to room temperature for 2 hours. After cooling, material samples (slabs or lenses) were examined using an Olympus microscope at 50-100× magnification set to determine bright-field microvacuoles (BF MVs) and dark-field microvacuoles (DF MVs).

Glass Transition Temperature

The glass transition temperatures (Tg) of materials in dry or fully-hydrated state were measured by differential scanning calorimetry at 10° C./minute, and was determined at the midpoint of the transition of the heat flux curve.

Refractive Index (RI)

The refractive index of the materials was measured using a Bausch & Lomb refractometer (Cat. #33.46.10) at 589 nm and 35° C. Test slab samples were hydrated in deionized water or BSS for a minimum of 24 hours, blotted dry, and then placed on the sample stage. Measurements were taken within 5 minutes of placing on stage.

Latent Haze

Latent haze was qualitatively measured using a Schott KL 2500 LCD light source. IOLs or rectangular test slabs (1×2×0.1 cm) were hydrated in BSS for a minimum of 24 hours. Hydrated samples were then immersed in a 35° C. water bath and illuminated at the highest intensity while rotating samples in the x, y, and z directions to determine the presence of latent haze. In general, hydrated materials are considered to have an unacceptable level of latent haze when the material becomes noticeably hazy in deionized water or BSS within 5 minutes at 35° C. and remains hazy for greater than 1 hour in the 35C bath. In most cases the haze is not permanent and molecular reorientation causes the material to become clear while at 35° C. Materials having an acceptable level of latent haze generally become clear within approximately 30 minutes of heating at 35° C. Materials considered to have no latent haze show no increase in haze when placed in the 35° C. bath.

Surface Tack

Tack testing was conducted on an Instron mechanical tester using a custom fixture for measuring the metal-polymer tack or adhesion. The fixture includes a highly polished stainless steel circular stationary pin of 8 mm in diameter that is affixed to the stationary portion of the load frame. The upper (moveable) section of the load frame crosshead is attached to a circular metal platform with a hole in the center. The moveable crosshead is lowered until the bottom pin appears through the hole in the center of the upper fixture and the crosshead movement is stopped when the pin is slightly above the metal platform. The polymer sample is then placed on the protruding pin. A fresh 10 mm diameter disk is press cut from the polymer sample and is placed on the top of the protruding pin. A 300 gram weight is placed on top of the sample, pressing the sample to the pin with a uniform load. One minute after placing the weight on the sample, the Instron mechanical tester is started with a separation rate of 5 mm/min. Data is collected at a rate of 5 points/sec until the sample is pulled up off of the pin. The maximum force and area under the curve (work energy) is recorded.

Surface-Light-Scatter Analysis

A Scheimpflug image-capture system was set up for consistent surface-light-scattering (SLS) analysis of IOLs. A purpose-designed dark eye model was assembled that would hold the IOL being examined and that could be filled with air or with a balanced salt solution (BSS, Alcon Laboratories, Inc.) at room temperature. Images of the model eye and IOL were captured with an EAS-1000 Anterior Segment Analysis System (Nidek Co. Ltd.) using the following settings: 200 W flash, 10.00 mm slit length, 0.08 mm slit width, and a fixed camera angle position 45 degrees from the light beam path. Surface-light-scattering densitometry was measured in computer-compatible-tape (CCT) units ranging from 0 (least intense) to 255 (most intense). SLS densitometry values were measured for anterior surfaces and posterior surfaces of the IOL along the axis of a line that crossed perpendicular to the center of the IOL optic. Peak scatter intensities were measured for anterior surfaces and posterior surfaces along the axis of 3 lines within the central 3.0 mm optic zone, yielding 6 measurements per IOL, which were then averaged. Surface light scattering was measured with IOLs dry, wetted (after approximately 2 minutes in a balanced salt solution), and hydrated (after 24 hours in a balanced salt solution).

Clarity

Sample clarity was qualitatively assessed on dry and hydrated lenses using a Dolan-Jenner Fiber-Lite Fiber Optic Illuminator (model 190). Hydrated lenses were placed in the light path while rotating the samples in the x, y, and z directions to determine relative haze.

Tensile Properties

For the determination of tensile properties of resultant materials, 8-12 mini-dogbones were cut from slab samples of each material tested, hydrated in BSS in microcentrifuge vials, and equilibrated to 18° C. in a water bath. Temperature controlled tensile testing was carried out using the Biopuls environmental chamber, which was mounted on the Instron 5943 Material Tester. The Biopuls chamber was regulated to 18° C. via circulating temperature controlled water bath. Just prior to testing mini-dogbones were removed from the 18° C. water bath and placed in the crossheads of the tensile tester. The Biopuls chamber was raised over the crossheads and samples further equilibrated for 2-min in the Biopuls chamber. Mini-dogbones were pulled at 50 mm/min rate to the breaking point to measure the tensile properties. Tensile strength (ultimate tensile stress), elongation at break (maximum strain), and Young's and secant modulus values were determined from the average of 8-12 runs per material formulation.

Injection Delivery Testing

Injection delivery testing through a Monarch-III D cartridge was performed for 2 IOLs from each formulation as follows. A Monarch-III D cartridge was opened and filled with Viscoat. A 40D SA60AT IOL (IOLs casted in 40 Dioper molds) derived from a formulation was loaded into the cartridge in accordance with the cartridge instructions for use. The cartridge was placed into the Monarch-III D handpiece and the plunger was advanced to the screw activated point and then slowly advanced further until the IOL was engaged. The IOL was advanced through the cartridge tip and into a dish of water. The IOL was observed to determine optic unfold time and the time for the haptics to completely release from the optic.

Furthermore, the IOL was observed under a microscope at 30× magnification for any damage that occurred on injection. As well, the cartridge tip was observed for stress marks or any breakage in the crown of the tip. If no IOL damage or cartridge tip damage was observed, then the delivery was considered to be passing. IOL or tip damage meant that the delivery run was a failure.

Chemicals

PEA=2-phenylethyl acrylate; DEGMBA=diethylene glycol monobenzyl ether acrylate nBAA=n-butylacrylamide; BMAA=N-butoxymethyacrylamide DMAA=N,N-dimethylacrylamide; NMAA=N-methylacrylamide HEAA=N-hydroxyethyl acrylamide; HEMA=hydroxyethyl methacrylate HEA=hydroxyethyl acrylate; HEAA=hydroxyethyl acrylamide AA=acrylamide; EGDMA=ethylene glycol dimethacrylate; BDDA=1,4-butanediol diacrylate; HMBAA=N,N-hexamethylenebisacrylamide;

WL-1=2-hydroxy-5-methoxy-3-(5-(trifluoromethyl)-2H-benzo[d][1,2,3]triazol-2-yl(benzyl methacrylate;

oMTP=2-(2H-benzo[d][1,2,3]triazol-2-yl)-4-methyl-6-(2-methylallyl)phenol

AL8739=N-[2-[4-hydroxy-3-[2-(2-methylphenyl)diazenyl]phenyl]ethyl] methacryamide AIBN=Azo-bis-(iso-butylnitrile); tBPO=tert-butyl peroxyoctoate Irgacure 819=phenylbis(2,4,6-trimethylbenzenoyl)phosphine oxide PEG=polyethylene glycol; Luperox A98=Benzoyl peroxide Perk=Perkadox 16 (Bis(tert-butylcyclohexyl) peroxydicarbonate)

Example 2

Formulations having compositions shown in Table 1 were prepared in glass vials and mixed well to fully dissolve all components. The ratio of nBAA over PEA is kept at about 0.67 for formulations 8A-8C, about 0.25 for formulations 12A-12C and 15A-15D.

TABLE 1

| | Concentration (parts by wt.) | | | | | | | | | |
|---|---|---|---|---|---|---|---|---|---|---|
| Component | 8A | 8B | 8C | 12A | 12B | 12C | 15A | 15B | 15C | 15D |
| nBAA | 39.2 | 37.2 | 35.0 | 19.1 | 17.2 | 15.3 | 16.5 | 15.44 | 14.7 | 13.5 |
| PEA | 58.5 | 55.6 | 53.0 | 78.6 | 75.2 | 72.6 | 66.1 | 61.93 | 58.0 | 54.3 |
| DMAA | 0.0 | 5.0 | 9.9 | 0.0 | 5.2 | 10.0 | 15.1 | 20.40 | 25.1 | 30.0 |
| EGDMA | 1.1 | 1.0 | 1.0 | 1.1 | 1.1 | 1.0 | 0 | 0 | 0 | 0 |
| BDDA | 0 | 0 | 0 | 0 | 0 | 0 | 1.0 | 1.0 | 1.0 | 1.0 |
| WL-1 | 1.2 | 1.2 | 1.2 | 1.2 | 1.2 | 1.2 | 1.2 | 1.23 | 1.2 | 1.2 |
| AIBN | 0.6 | 0.6 | 0.6 | 0.5 | 0.5 | 0.5 | 0.5 | 0.52 | 0.5 | 0.5 |

The prepared formulations were then filtered through 0.2 µm syringe filters into fresh vials, degassed with nitrogen, and cast in air atmosphere into untreated polypropylene slab molds or molds (net shaped 21D SN60WF and 40D SA60AT IOL lens wafers) and thermally cured. For formulations 8A-8C, three curing regime were used: (1) 90° C. for one hour and then 110° C. for one hour; (2) 70° C. for 15 hours, then 100° C. for one hour, and finally 110° C. for one hour; and (3) 70° C. for 3 hours, then 90° C. for one hour, and finally 110° C. for one hour. For formulations 12A-12-C, curing was performed as following: 70° C. for 20 hours and then 110° C. for 3 hours. For formulations 15A-15D, curing was performed as following: 70° C. for 3 hours, then 90° C. for one hour, and finally 110° C. for one hour.

Following thermal curing, samples were demolded and extracted initially with ethanol (unless another solvent is listed) at room temperature (21-23° C.) for usually 16-20 hours. After extraction, samples were slowly air dried for at least 6-8 hours, then in a vacuum oven at 60-70° C. under 30 inches of Hg vacuum for at least 16 hours.

Extractables %, EWC %, BF MV's, DF MV's, and hydrated RI at room temperature (RT) were determined according to the procedures described in Example 1. The results are reported in Table 2.

The prepared formulations were then filtered through 0.2 µm syringe filters into fresh vials, degassed with nitrogen, and cast in air atmosphere into untreated polypropylene slab molds or molds (net shaped 21D SN60WF and 40D SA60AT IOL lens wafers) stored in air and thermally cured (30-70° C. for 15 minutes, 70° C. for 3 hours, 70-90° C. for 10 minutes, 90° C. for one hour, 90-110° C. for 10 minutes, and 110° C. for one hour).

Following thermal curing, samples were demolded and extracted initially with ethanol (unless another solvent is listed) at room temperature (21-23° C.) for usually 16-20 hours. After extraction, samples were slowly air dried for at least 6-8 hours, then in a vacuum oven at 60-70° C. under 30 inches of Hg vacuum for at least 16 hours.

Extractables %, EWC %, BF MV's, DF MV's, tensile properties, glass transition temperature, surface tack, surface light scattering were determined according to the procedures described in Example 1. Injection delivery testing was performed according the procedure described in Example 1.

All the resultant materials were glassy and tack testing at room temperature in dry state indicated values well below 1 N, which was much lower than the passing criteria of 30 N.

TABLE 2

| Properties | Corresponding Formulation | | | | | | | | | |
|---|---|---|---|---|---|---|---|---|---|---|
|  | 8A | 8B | 8C | 12A | 12B | 12C | 15A | 15B | 15C | 15D |
| % Extractables | 8.93* | 10.44* | 12.84* | 9.58 | 8.01 | 7.81 | 2.86 | 2.96 | 4.84 | 2.72 |
| SD | 0.82 | 0.58 | 0.11 | 1.13 | 0.86 | 0.37 | 0.57 | 1.06 | 0.40 | 0.26 |
| BF MV | Fail | Fail | Fail | Fail | Fail | Fail | Few | ND | ND | ND |
| DF MV |  |  |  |  |  |  | Many | Many | <10 | <10 |
| Clarity#, | cloudy | cloudy | cloudy | cloudy | cloudy | cloudy | clear | clear | clear | clear |
| EWC 35° C. | 3.36 | 3.64 | 4.11 | 2.14 | 2.49 | 2.74 | 4.09 | 5.10 | 6.37 | 7.93 |
| After MV test | 3.91 | 4.22 | 4.59 |  |  |  |  |  |  |  |
| Hydrated RI |  |  |  |  |  |  | 1.5385 | 1.5370 | 1.5264 | 1.5215 |

ND = not detected;
*extractable calculated from the 3$^{rd}$ curing regime;
clarity post MV tests.

Example 3

Formulations having compositions shown in Table 3 were prepared in glass vials and mixed well to fully dissolve all components.

TABLE 3

|  | Conc. (parts by wt.) | | | |
|---|---|---|---|---|
| Component | 88A | 88B | 88C | 88D |
| nBAA | 15.4 | 14.4 | 13.4 | 13.4 |
| PEA | 61.5 | 57.5 | 53.5 | 53.5 |
| DMAA | 20 | 25 | 30 | 30 |
| BDDA | 1.0 | 1.0 | 1.0 | 1.0 |
| oMTP | 1.8 | 1.8 | 1.8 | 1.8 |
| AIBN | 1.0 | 1.0 | 1.0 | 1.0 |

The glass transition temperature (Tg) for the materials derived from 88C and 88D were found to be 28° C. in the dry state and about 4° C. in the hydrated state.

Injection testing of 40D SA60AT net shaped IOLs prepared from each formulation was successfully delivered through a Monarch-III D-cartridge with minimal or no stress marks observed on the cartridge tip. So that the injection of 40D SA60AT IOLs comprised of these materials approximated injection through a 2-mm incision and the injection criteria was met.

Preliminary surface light scattering at 1.4 years aged gave 33 CCT on the anterior surface and 25 CCT on the posterior for sample 88D.

The results are reported in Table 4.

TABLE 4

|  | Formulation | | | |
|---|---|---|---|---|
|  | 88A | 88B | 88C | 88D |
| % Exactables by EtOH | 3.11 ± 0.26 | 3.28 ± 0.49 | 3.40 ± 0.32 | 2.65 ± 0.19 |
| EWC, 35° C./BSS | 4.98 ± 0.13 | 6.90 ± 0.08 | 8.00 ± 0.15 | 8.80 ± 0.02 |
| Hydrated RI, BSS, RT | 1.5338 ± 0.0010 | 1.5286 ± 0.0005 | 1.5217 ± 0.0001 | 1.5217 ± 0.0002 |
| Clarity | clear | clear | clear | clear |
| BF MV's | none | none | none | none |

TABLE 4-continued

| | Formulation | | | |
|---|---|---|---|---|
| | 88A | 88B | 88C | 88D |
| DF MV's, per area | ~10 | <10 | <10 | <10 |
| Tensile strength (MPa) | 7.83 ± 0.50 | 6.50 ± 0.62 | 4.27 ± 0.72 | 3.42 ± 0.46 |
| Elongation at break (%) | 387 ± 13 | 376 ± 27 | 341 ± 17 | 317 ± 24 |
| Young's Modulus (MPa) | 16.6 ± 3.98 | 30.9 ± 10.1 | N/A | N/A |
| 50% Secant Modulus (MPa) | 1.60 ± 0.09 | 1.60 ± 0.09 | 1.06 ± 0.08 | 1.13 ± 0.15 |
| 100% Secant Modulus (MPa) | 1.04 ± 0.05 | 1.07 ± 0.06 | 0.72 ± 0.05 | 0.75 ± 0.11 |

N/A = Young's modulus data could not be calculated accurately and was not available Tensile properties were determined on hydrated samples at 18° C., which approximates operating room temperature. In general the tensile strength and elongation at break, and 50% and 100% secant moduli seemed to follow a trend of lower values at increasing water content. However, the elongation at break was quite high ranging from 317 to 387%, which is over 200% higher than an AcrySof Natural as control (Tensile strength=8.99±1.08 MPa; Elongation at break=118±7%; Young's Modulus=150±48 MPa; 100% Secant Modulus=7.16±0.27 MPa). In fact, all values indicate a much softer and deformable materials in all the resultant materials above than seen with AcrySof Natural.

Example 4

Formulations having compositions shown in Table 5 were prepared in glass vials and mixed well to fully dissolve all components.

TABLE 5

| | Concentration (parts by wt) | | | | |
|---|---|---|---|---|---|
| Component | 92A | 92B | 92C | 92D | 92E |
| PEA | 53.5 | 53.1 | 52.7 | 52.3 | 51.9 |
| nBAA | 13.4 | 13.3 | 13.2 | 13.1 | 13.0 |
| DMAA | 30 | 30 | 30 | 30 | 30 |
| BDDA | 1.0 | 1.5 | 2.0 | 2.5 | 3.0 |
| oMTP | 1.8 | 1.8 | 1.8 | 1.8 | |
| tBPO | 1.5 | 1.5 | 1.5 | 1.5 | 1.5 |

The prepared formulations were then filtered through 0.2 μm syringe filters into fresh vials, degassed with nitrogen, and cast in air atmosphere into untreated polypropylene slab molds or molds (net shaped 21D SN60WF and 40D SA60AT IOL lens wafers) stored in air and thermally cured (30-70° C. for 15 minutes, 70° C. for 3 hours, 70-90° C. for 10 minutes, 90° C. for one hour, 90-110° C. for 10 minutes, and 110° C. for one hour).

Following thermal curing, samples were demolded and extracted initially with ethanol (unless another solvent is listed) at room temperature (21-23° C.) for usually 16-20 hours. After extraction, samples were slowly air dried for at least 6-8 hours, then in a vacuum oven at 60-70° C. under 30 inches of Hg vacuum for at least 16 hours.

Extractables %, EWC %, BF MV's, DF MV's, tensile properties, glass transition temperature, surface tack, surface light scattering were determined according to the procedures described in Example 1. Injection delivery testing was performed according the procedure described in Example 1.

All the resultant materials were glassy and tack testing at room temperature in dry state indicated values well below 1 N, which was much lower than the passing criteria of 30 N. The results are reported in Table 6.

TABLE 6

| | Formulation | | | | |
|---|---|---|---|---|---|
| | 92A | 92B | 92C | 92D | 92E |
| % Exactables by acetone | 0.90 ± 0.52 | 0.94 ± 0.58 | 2.37 ± 0.95 | 1.08 ± 0.37 | 2.30 ± 0.80 |
| EWC, 35° C./BSS | 7.84 ± 0.83 | 5.54 ± 1.14 | 7.67 ± 0.08 | 6.75 ± 0.31 | 6.52 ± 0.39 |
| Clarity | clear | clear | clear | clear | clear |
| BF MV's | none | none | none | none | none |
| DF MV's, per area | none | none | none | none | none |
| Injection for Micro Incision | pass | pass | fail | fail | Fail |
| Surface Light Scattering | Not tested | hydrated | | | |
| Tensile strength (MPa) | 5.00 ± 1.01 | 6.12 ± 1.39 | 5.22 ± 1.07 | 5.12 ± 0.37 | 4.69 ± 0.48 |
| Elongation at break (%) | 299 ± 14 | 225 ± 27 | 192 ± 14 | 165 ± 10 | 139 ± 13 |
| Young's Modulus (MPa) | 30.6 ± 7.3 | 28.4 ± 5.3 | 26.5 ± 3.6 | 30.2 ± 3.3 | 32.8 ± 3.4 |
| 50% Secant Modulus (MPa) | 3.32 ± 0.07 | 3.59 ± 0.10 | 3.87 ± 0.08 | 3.99 ± 0.23 | 3.58 ± 1.03 |
| 100% Secant Modulus (MPa) | 2.06 ± 0.04 | 2.33 ± 0.08 | 2.67 ± 0.07 | 2.92 ± 0.20 | 2.95 ± 0.60 |
| Controls: | | | | | |
| | Tensile strength (MPa) | Elongation at break (%) | Young's modulus (MPa) | 50% Secant Modulus (MPa) | 100% Secant Modulus (MPa) |
| AcrySof: | 10.19 ± 1.29 | 113 ± 9 | 158 ± 18 | 9.39 ± 0.96 | 8.65 ± 0.43 |
| AcrySof 2: | 3.29 ± 0.52 | 111 ± 16 | 111 ± 16 | 2.40 ± 0.3 | 2.23 ± 0.97 |

The % extractables varied from 0.90 (92A) to 2.37% (92D) with no trend relating to composition and were all <3%, which is usually considered desirable. If 92B is disregarded the water content shows a mild trend towards decreasing water content with increasing crosslinker.

Microvacuole performance was good across the board with all formulations (92A-D) showing no BF or DF MV's. All formulations were clear and transparent and glassy in dry state at room temperature, indicating that surface tack would not be an overwhelming issue on demolding and handling.

Formulations 92A-D generally showed little to no latent haze when equilibrated in water at 23° C. and then immersed in a water bath at 35° C.

Injection performance provided an important trend to further titrate the crosslinker level for this material. On injection through a Monarch-III D-cartridge, formulations 92C, 92D, & 92E all caused a crack in the cartridge tip. Formulation 92A left no stress marks on the cartridge and 92B only moderate stress marks with no breakage of the tip. Consequently, at 2% and higher levels of BDDA crosslinker, the injection performance was compromised. Therefore, no surface light scattering data was determined on 92A, 92C, 92D, or 92E, but only on 92B. The surface light scattering data for the hydrated material derived from formulation 92B is as follows: 19±11 CCT at zero year aging; 36±28 CCT at 1-year aging; 37±23 CCT at 5-years aging; 60±55 CCT at 10-years aging.

Tensile properties were determined on all the 92-formulation series. Since 92A is a repeat formulation of 88D, it appears that the 92A is somewhat higher in secant modulus (50% & 100%) and tensile strength (ultimate tensile stress), but lower in elongation at break (299 vs. 317%). Even so, within the 92-series the most obvious trend was that the values of elongation at break decreased with increasing crosslinker concentration. With the tensile strength, Young's modulus, and 50% secant moduli, no clearly defined trend was found in the data. With the 100% secant modulus a mild trend in increasing values was observed with increasing crosslinker concentration.

Example 5

Formulations having compositions shown in Table 7 were prepared in glass vials and mixed well to fully dissolve all components. Formulations 8-5B and 8-5A were of nearly identical composition, but the 1st run when using formulation 8-5A yielded slabs and only a few IOLs, whereas the 1st run when using formulation 8-5B yielded a good group of 21 & 40D IOLs suitable for testing, so that both of these two formulations are mixed together.

TABLE 7

| Compo- | Concentration (parts by wt.) | | | | | | |
|---|---|---|---|---|---|---|---|
| nent | 8-5B | 8-5A | 8-6A | 8-8 | 8-9 | 8-21 | 8-27 |
| PEA | 53.28 | 53.29 | 53.49 | 53.6 | 53.7 | 53.7 | 53.7 |
| nBAA | 13.24 | 13.29 | 13.38 | 13.4 | 13.4 | 13.4 | 13.4 |
| DMAA | 30.09 | 30.13 | 30.32 | 30.1 | 30.0 | 30.0 | 30.0 |
| BDDA | 1.59 | 1.48 | 1.01 | 1.04 | 1.04 | 1.03 | 1.04 |
| oMTP | 1.81 | 1.81 | 1.81 | 1.81 | 1.81 | 1.81 | 1.81 |
| AL8739 | | | 0.041 | 0.040 | 0.040 | 0.040 | |
| tBPO | 1.73 | 1.50 | | | | | |
| Irgacure 819 | | | 0.53 | 0.50 | 0.30 | 0.31 | |

The prepared formulations were then filtered through 0.2 μm syringe filters into fresh vials, degassed with nitrogen, and cast in air atmosphere into polypropylene slab molds or IOL molds (net shaped 21 D SN60WF and 40D SA60AT IOL lens wafers) degassed in a glove box. The curing regimes are as following: Formulations 8-5A, 8-5B and 8-27 were thermally cured, cast in glove box, degassed molds (30-70° C. for 15 minutes, 70° C. for 3 hours, 70-90° C. for 10 minutes, 90° C. for one hour, 90-110° C. for 10 minutes, and 110° C. for one hour); formulations 8-6A, 8-8, 8-9, and 8-21 were blue light cured at 55° C. for 1 hour using a super actinic fluorescent bulb with output of approximately 4 mW/cm$^2$ at 400-440 nm. Photocured samples were cured single sidedly with radiation entering the sample from one side.

Following curing, samples were demolded and extracted initially with ethanol (unless another solvent is listed) at room temperature (21-23° C.) for usually 16-20 hours. After extraction, samples were slowly air dried for at least 6-8 hours, then in a vacuum oven at 60-70° C. under 30 inches of Hg vacuum for at least 16 hours.

Extractables %, EWC %, BF MV's, DF MV's, tensile properties, glass transition temperature, surface tack, surface light scattering were determined according to the procedures described in Example 1. Injection delivery testing was performed according the procedure described in Example 1. The results are reported in Table 8.

TABLE 8

| | Formulation | | | | | |
|---|---|---|---|---|---|---|
| | 8-5A&5B | 8-6A | 8-8 | 8-9 | 8-21 | 8-27 |
| Tack, pre-extracted | glassy | glassy | glassy | glassy | glassy | glassy |
| Tack, post-extracted | N.T. | N.T. | N.T. | N.T. | N.T. | N.T. |
| Tack, post-plasma treated | N.T. | N.T. | N.T. | N.T. | N.T. | N.T. |
| Clarity | clear | clear | clear | clear | clear | |
| % transmittance @ 550 nm | 98.6% | 99.4% | 98.3 | 98.7 | | |
| UV block, 21D SN60WF 10% T cutoff wavelength | 396 nm | 395 nm | 397.5 nm | 398 nm | | |

TABLE 8-continued

| | Formulation | | | | | |
|---|---|---|---|---|---|---|
| | 8-5A&5B | 8-6A | 8-8 | 8-9 | 8-21 | 8-27 |
| % Exactables, slabs, % | 2.34 ± 0.17 (n = 4) | | 1.41 ± 0.14 (n = 4) | 1.57 ± 0.26 (n = 4) | 1.73 ± 0.38 (n = 4) | 2.93 ± 0.79 (n = 4) |
| % Exactables, IOL, % | N.T. | 3.42 | 3.32 | 3.34 ± 0.62 (n = 2) | 4.10 ± 0.81 (n = 2) | 3.23 ± 0.00 (n = 2) |
| BF MV's, count per screen (n = samples × areas viewed) | None (n = 1) | None (n =1) | None (n = 3 × 3) | None (n = 3 × 3) | None (n = 3 × 3) | None (n = 3 × 3) |
| DF MV's, count per screen (n = samples × areas viewed) | <3 (n = 1) | <3 (n =1) | Ave. 3 (n = 3 × 3) | Ave. 1 (n = 3 × 3) | <1 (n = 3 × 3) | Ave. 1.1 (n = 3 × 3) |
| EWC %, 35° C./BSS (n = 4) | 8.41 ± 0.10 | N.T. | 8.41 ± 0.16 | 8.33 ± 0.32 | 7.98 ± 0.02 | 8.15 ± 0.12 |
| Hydrated RI, RT & BSS | 1.5240 | N.T. | 1.5259 | 1.5255 | 1.5250 | 1.5256 |
| Tensile Strength (MPa) | 3.35 ± 0.48 (n = 5) | | 3.93 ± 0.78 (n = 7) | 2.72 ± 0.56 (n = 7) | 2.13 ± 0.26 (n = 9) | N.T. |
| Elongation at break (%) | 224 ± 14.6 (n = 5) | | 304 ± 17 (n = 7) | 274 ± 23 (n = 7) | 240 ± 23 (n = 9) | |
| Young's Modulus (MPa) | 7.66 ± 2.14 (n = 5) | | 14.15 ± 5.92 (n = 6) | 25.61 ± 11.81 (n = 5) | 12.56 ± 6.22 (n = 8) | |
| 50% Secant Modulus (MPa) | 1.46 ± 0.06 (n = 5) | | 1.27 ± 0.08 (n = 7) | 1.14 ± 0.06 (n = 7) | 1.24 ± 0.10 (n = 9) | |
| 100% Secant Modulus (MPa) | 1.10 ± 0.04 (n = 5) | | 0.89 ± 0.05 (n = 7) | 0.83 ± 0.04 (n = 7) | 0.87 ± 0.05 (n = 9) | |

These materials continued to show the good properties previously found for acrylamide based IOL materials: low surface tack due to their high Tg (28° C.) making them glassy at room temperature; low extractables between 1.4-3.4% for slabs and between 3.2-4.1% for IOLs; no BF microvacuoles and 3 DF microvacuoles or less per viewing area, well below <10 criteria; EWC of 8.0 to 8.4% while still maintaining a high hydrated RI of 1.524 to 1.526 at 35° C.; desirable tensile profile for micro-incision with elongation at break ranging from 240-304% and low 100% secant modulus from 0.83-0.89 MPa (with 1.0% BDDA) indicating a highly deformable material; passing results in lab testing for injection of hydrated 40D SA60AT IOL facsimiles through Monarch 111-D cartridges, including successful 20-min dwell time; and delivery testing through D-cartridges showed low injection force measurements of <10 N (all) and usually <6 N (IOLs derived from formulations 8-5B (8-5A), 8-6A, 8-8, & 8-9), as well as, low incidence of optic or haptic damage from injection.

It is observed that, upon delivery through the Monarch-III D-cartridge, the haptics of 40D IOLs derived from formulation 8-5B (8-5A) and argon-plasma-treated did not stick to the IOL optics whereas the haptics of 40D IOLs from formulations 8-6A, 8-8, 8-9, & 8-21 and without plasma treatment tended to stick to the IOL optic as seen for formulations 6A, 8, 9, & 21 and took as long as 5-minutes to release. After 40D IOLs derived from formulation 8-9 were also submitted for argon plasma treatment, only 1 of 6 IOLs had haptics stuck to the optic, but it only took 1-sec to release. Therefore, the haptic stick issue can be resolved by processing IOLs through argon plasma treatment.

Table 9 shows the surface light scattering (SLS) data on samples from time zero with aged samples from 1 to 10 yrs.

TABLE 9

| | Formulation | | | | | |
|---|---|---|---|---|---|---|
| | 8-5A&5B | 8-6A | 8-8 | 8-9 | 8-21 | 8-27 |
| SLS @ t = 0, Hydrated, CCT (n = 3) | 3.5 ± 3.9 | 1.4 ± 1.6 | 5.7 ± 2.4 | 24.7 ± 12.0 | 18.3 ± 9.4** | 2.6 ± 2.3** |
| SLS @ 1 yr, Hydrated, CCT (n = 3) | 4.9 ± 3.0 | 8.7 ± 5.8 | 20.4 ± 9.2** | 25.7 ± 13.3** | 11.7 ± 9.4** (n = 2) | 38.4 ± 18.2** 1.5 yrs |
| SLS @ 3 yrs, Hydrated, CCT (n = 3) | | 11.0 ± 9.0 | | | | |
| SLS @ 5 yrs, Hydrated, CCT (n = 3) | 21.5 ± 6.5 | | 74.8 ± 9.6** | 85.1 ± 20.7** | 44.5 ± 9.8** | 37.3 ± 19.4** 6 yrs |
| SLS @ 10 yrs, Hydrated, CCT (n = 3) | 40.8 ± 32.6 | 58.4 ± 25.6** | 51.5 ± 12.6** | 55.2 ± 22.9** | 39.4 ± 8.7 | 26.6 ± 8.5** |

**mild bulkhaze observed

Example 6

Formulations having compositions shown in Table 10 were prepared in glass vials and mixed well to fully dissolve all components.

The prepared formulations were then filtered through 0.2 μm syringe filters into fresh vials, degassed with nitrogen, and cast in air atmosphere into polypropylene slab molds or molds (net shaped 21 D SN60WF and 40D SA60AT IOL lens wafers) degassed in a glove box. The curing regimes are as following: all the formulations except formulation 29B+ were blue light cured at 55° C. for 1 hour in air and in degassed molds; formulation 29B+ was first blue light cured at 55° C. for 1 hour in air and in degassed molds and then post-cured thermally at 100° C. for 2 hours.

TABLE 10

| Component | 29B | 29B+ | 29C | 29D | 29E | 29F |
|---|---|---|---|---|---|---|
| | Concentration (parts by wt.) | | | | | |
| PEA | 52.59 | 52.59 | 53.17 | 59.70 | 60.3 | 53.20 |
| nBAA | 14.01 | 14.01 | 14.02 | 7.00 | 7.0 | 14.01 |
| DMAA | 30.05 | 30.05 | 29.97 | 29.99 | 30.0 | 29.96 |
| HMBAA | 1.49 | 1.49 | 1.03 | 1.52 | 0.50 | |
| BDDA | 0 | 0 | 0 | 0 | 1.00 | 0.52 |
| oMTP | 1.86 | 1.86 | 1.80 | 1.80 | 1.71 | 1.80 |
| tBPO | | 0.10 | | | | |
| Irgacure 819 | 0.30 | 0.30 | 0.30 | 0.30 | 0.30 | 0.30 |
| | Properties | | | | | |
| Tack, pre-extracted | glassy | glassy | glassy | glassy | glassy | glassy |
| Clarity | clear | clear | clear | clear | clear | |
| % Exactables, slabs, % | 2.29 ± 0.35 (n = 3) | 1.89 ± 0.15 (n = 4) | 1.92 ± 0.19 (n = 4) | 1.35 ± 0.22 (n = 4) | 2.58 ± 0.22 (n = 4) | 2.72 ± 0.04 (n = 4) |
| % Exactables, IOL, % | 3.23 ± 0.00 (n = 2) | 2.21 | 4.15 | 3.16 ± 0.92 (n = 2) | 15.79 | 13.2 |

Following curing, samples were demolded and extracted initially with ethanol (unless another solvent is listed) at room temperature (21-23° C.) for usually 16-20 hours. After extraction, samples were slowly air dried for at least 6-8 hours, then in a vacuum oven at 60-70° C. under 30 inches of Hg vacuum for at least 16 hours.

Extractables %, EWC %, BE MV's, DE MV's, tensile properties, glass transition temperature, surface tack, surface light scattering were determined according to the procedures described in Example 1. Injection delivery testing was performed according the procedure described in Example 1.

The results of extractables %, EWC %, tack prior to extraction, and clarity are reported in Table 10.

Several formulations quickly crashed out of the study due to poor SS results at 1-yr. aging (29° C.) or poor clarity on re-hydration after drying from extraction (Formulations 29B+, 29E, & 29F), so that only formulations 29B and 29D were left in the study. However, 29B had high SS values at 0.9 & 10-yrs. aging (>30 CCT), but 29D was consistently below the criteria limit of 30 CCT at all aging time points. Therefore, further data was gathered on 29D and it was found to have 7.4% water content, a high RI of 1.528, no BF microvacuoles, and DF microvacuoles (average 1.1) well below the 10 per viewing area. As well, 40D SA60AT IOLs of the 29D material passed the injection criteria through a D-cartridge with a 20-min dwell time. The only composition difference between the 29D composition and some of the previous acrylamide materials, like formulations 8-5B (8-5A) and 8-6A in Example 5 was the replacement of BDDA with the bis-acrylamide crosslinker.

Example 7

Formulations were prepared in glass vials by thoroughly mixing 997% by weight of each of the compositions listed in Tables 11 and 12 with 0.30% by weight of Irgacure 819.

TABLE 11

| | Concentration (parts by wt.) | | | | | | |
|---|---|---|---|---|---|---|---|
| Component | 35A | 35B | 35C | 35D | 35E | 35F | 35G |
| PEA | 53.90 | 61.89 | 64.93 | 65.19 | 53.84 | 53.64 | 53.68 |
| nBAA | 8.02 | 0 | 0 | 0 | 8.42 | 0 | 8.35 |
| DMAA | 29.98 | 30.03 | 20.07 | 19.94 | 29.91 | 28.37 | 30.07 |
| HEMA | 5.06 | 5.04 | 11.98 | 12.07 | 0 | 0 | 5.13 |
| HEAA | 0 | 0 | 0 | 0 | 5.07 | 15.13 | 0 |
| HMBAA | 0 | 0 | 0 | 0 | 0 | 0 | 1.03 |
| BDDA | 1.24 | 1.23 | 1.23 | 1.01 | 0.98 | 1.05 | 0 |
| oMTP | 1.81 | 1.80 | 1.80 | 1.79 | 1.78 | 1.81 | 1.74 |

TABLE 12

| Component | Concentration (parts by wt.) | | | | | | |
|---|---|---|---|---|---|---|---|
| | 35H | 35I | 35J | 35K | 35L | 35M | 35N |
| PEA | 53.70 | 53.72 | 53.66 | 53.66 | 53.74 | 53.77 | 53.48 |
| nBAA | 0 | 3.46 | 8.59 | 0 | 3.47 | 0 | 13.43 |
| DMAA | 28.53 | 30.08 | 29.95 | 28.49 | 30.06 | 28.50 | 30.02 |
| HEMA | 14.97 | 9.98 | 0 | 0 | 0 | 15.02 | 0 |
| HEAA | 0 | 0 | 5.00 | 15.04 | 9.92 | 0 | 0 |
| HMBAA | 1.00 | 0.52 | 0.99 | 0.99 | 0.50 | 0 | 0 |
| BDDA | 0 | 0.45 | 0 | 0 | 0.46 | 0.95 | 1.26 |
| oMTP | 1.79 | 1.79 | 1.80 | 1.82 | 1.84 | 1.76 | 1.81 |

The prepared formulations were then filtered through 0.2 μm syringe filters into fresh vials, degassed with nitrogen, and cast in air atmosphere into polypropylene slab molds or molds (net shaped 21D SN60WF and 40D SA60AT IOL lens wafers) degassed in a glove box. Formulations 35A-35C and 35E-35N were blue light cured at 55° C. for 1 hour in air and in degassed molds as previously described. Formulation 35D was not cast.

Following curing, samples were demolded and extracted initially with ethanol (unless another solvent is listed) at room temperature (21-23° C.) for usually 16-20 hours. After extraction, samples were slowly air dried for at least 6-8 hours, then in a vacuum oven at 60-70° C. under 30 inches of Hg vacuum for at least 16 hours.

Extractables %, EWC %, BF MV's, DF MV's, tensile properties, glass transition temperature, surface tack, surface light scattering were determined according to the procedures described in Example 1. Injection delivery testing was performed according the procedure described in Example 1. The results of extractables %, EWC %, tack prior to extraction, and clarity are reported in Tables 13-15.

TABLE 13

| | Formulation | | | | | |
|---|---|---|---|---|---|---|
| | 35A | 35B | 35C | 35E | 35F | 35G |
| Extractables %, slab | 1.18 ± 0.39 | 0.77 ± 0.18 | 0.63 ± 0.24 | 1.84 ± 0.56 | 1.24 ± 0.43 | 2.44 ± 1.05 |
| SS, hydrated @ 2 yrs | 32.33 ± 8.33 | 32.44 ± 11.29 | 14.89 ± 2.72 | 38.94 ± 0.56 | 32.25 ± 9.01 | 21.22 ± 5.35 |
| SS, hydrated @ 5 yrs | 41.9 ± 12.4 | 36.0 ± 12.9 | 26.8 ± 9.8 | 61.0 ± 17.3 | 47.2 ± 4.9 | 25.8 ± 4.4 |
| SS, hydrated @ 10 yrs | 30.6 ± 6.8 | 27.4 ± 8.0 | 21.4 ± 4.0 | Not tested | Not tested | 41.9 ± 4.6** |

TABLE 14

| | Formulation | | | | |
|---|---|---|---|---|---|
| | 35H | 35I | 35J | 35K | 35L |
| Extractables %, slab | 1.20 ± 0.43 | 2.15 ± 0.71 | 2.19 ± 0.57 | 1.68 ± 0.24 | 3.61 ± 0.84 |
| SS, hydrated @ 2 yrs | 28.28 ± 29.09 | 17.00 ± 6.14 | 46.00 ± 12.35 | 28.39 ± 16.43 | 37.78 ± 20.61 |
| SS, hydrated @ 5 yrs | 9.9 ± 2.0 | 12.4 ± 3.6 | Not tested | 30.7 ± 10.5 | 19.9 ± 2.3 |
| SS, hydrated @ 10 yrs | 15.7 ± 4.6 | 9.5 ± 3.9 | Not tested | 14.4 ± 2.4 | 53.2 ± 7.0** |

TABLE 15

| | Formulation | |
|---|---|---|
| | 35M | 35N |
| Extractables %, slab | 1.66 ± 0.0.14 | 2.66 ± 0.73 |
| SS, hydrated @ 2 yrs | 11.58 ± 0.90 | 33.00 ± 7.07 |
| SS, hydrated @ 5 yrs | 9.5 ± 2.4 | 46.7 ± 7.0 |
| SS, hydrated @ 10 yrs | 12.5 ± 2.9 | Not tested |

Out of 13 formulations prepared in the 35 series, 6 had passing SS tests at the 10-yr. aging time point. Only one material passing SS in the 35 series had HEAA at 15% (35K), the other 5 passing materials contained HEMA (35B, 35C, 35H, 35I, & 35M) and all of these had 10-15% HEMA, except 35B (5% HEMA). Even though 6 formulations passed SS test (<30 CCT) after 10-yrs aging, one formulation (35B) had inconsistent SS results (>30 CCT) at 2 and 5 yrs.

Overall, these results indicate that formulation adjustment, which incorporates a surface-distributed hydrophilic methacrylate, like HEMA, is the most reliable way to improve surface light scattering (35B, 35C, 35H, 35I, & 35M). However, minor changes in crosslinker to a more hydrolysis-resistant bis-acrylamide crosslinker can also improve SS results (29D) in Example 6. And finally, the improved processing of inert casting into degassed molds (Example 5) was enough to render one of the base formulations (8-27) passing after 10-yrs. aging, whereas analogous blue light cured formulations (8-8, 8-9, & 8-21) all had SS results >30 CCT after 10-yrs. aging.

Example 8

Formulations having compositions shown in Table 16 were prepared in glass vials and mixed well to fully dissolve all components. The prepared formulations were then filtered through 0.2 μm syringe filters into fresh vials, degassed with nitrogen, and cast in air atmosphere into polypropylene slab molds or molds (net shaped 21D SN60WF and 40D SA60AT IOL lens wafers). Formulations were thermally cured, cast in air, molds which have not been degassed to remove surface oxygen as following: 30-70° C. for 15 minutes, 70° C. for 3 hours, 70-90° C. for 10 minutes, 90° C. for one hour, 90-110° C. for 10 minutes, and 110° C. for one hour).

TABLE 16

| | Conc. (parts by wt.) | |
|---|---|---|
| Component | 47-1 | 47-2 |
| PEA | 52.0 | 52.1 |
| DMAA | 29.4 | 29.5 |
| BMAA | 15.8 | 15.9 |
| BDDA | 1.09 | |
| HMBAA | | 1.12 |
| oMTP | 1.7 | 1.3 |
| tBPO | 1.34 | 1.30 |

Following curing, samples were demolded and extracted initially with ethanol (unless another solvent is listed) at room temperature (21-23° C.) for usually 16-20 hours. After extraction, samples were slowly air dried for at least 6-8 hours, then in a vacuum oven at 60-70° C. under 30 inches of Hg vacuum for at least 16 hours.

Surface light scattering were determined according to the procedures described in Example 1. The results are reported in Table 17.

TABLE 17

| | Formulation | |
|---|---|---|
| | 47-1 | 47-2 |
| SLS @ t = 0, Dry, CCT (n = 3) | 13.2 ± 28.2 | 3.3 ± 2.8 |
| SLS @ t = 0, wetted, CCT (n = 3) | 3.0 ± 3.3 | 2.3 ± 1.4 |
| SLS @ t = 0, hydrated, CCT (n = 3) | 5.3 ± 8.1 | 2.3 ± 1.1 |
| SLS @ 1 yr, Dry, CCT (n = 3) | 6.4 ± 4.0 | 12.9 ± 7.5 |
| SLS @ 1 yr, wetted, CCT (n = 3) | 3.6 ± 1.9 | 5.8 ± 5.3 |
| SLS @ 1 yr, hydrated, CCT (n = 3) | 4.9 ± 1.9 | 8.0 ± 5.1 |
| SLS @ 5 yrs, Dry, CCT (n = 3) | 5.2 ± 7.7 | 2.7 ± 2.3 |
| SLS @ 5 yrs, wetted, CCT (n = 3) | 5.1 ± 2.4 | 4.7 ± 1.6 |
| SLS @ 5 yrs, hydrated, CCT (n = 3) | 27.9 ± 6.3 | 17.4 ± 4.2 |
| SLS @ 10 yrs, Dry, CCT (n = 3) | 5.4 ± 3.8 | 7.3 ± 4.2 |
| SLS @ 10 yrs, wetted, CCT (n = 3) | 5.7 ± 1.9 | 7.3 ± 1.6 |
| SLS @ 10 yrs, hydrated, CCT (n = 3) | 18.9 ± 4.4 | 13.0 ± 3.1 |

BMAA = N-butoxymethyacrylamide

Example 9

Acrylic materials with high acrylamide monomer concentration can display a lower critical solution temperature (LOST) limit, which causes continuous haze and phase separation in hydrated materials in heating from RT to an elevated temperature above the LOST. Copolymers of N-isopropylacrylamide (NIPAM) are well-known for this behavior, which is characterized by the release of bound water molecules from the loss of hydrogen bonding and hydrophobic association within the polymer matrix. This phenomenon leads to phase separation and can cause these materials to become hazy and lose clarity. Many of the acrylamide-based IOL materials described above exhibit a similar phenomenon that results in an intermittent form of this behavior in heating a hydrated IOL from RT to 35° C., becoming hazy and losing clarity above the "LSCT" or latent haze transition temperature for a finite period of time as described in Example 1. This phenomenon in the acrylamide-based IOL materials is temporary, lasting from a few minutes to 24 hours or more after heating to 35° C. However, this temporary haze can be a serious issue for a wet-packed IOL material during the development stage, in addition to the patient upon implantation.

The following example illustrates how to eliminate the latent haze limit that causes intermittent haze and phase separation in hydrated IOLs in heating from RT to 35° C. The simplest solution to this issue is to reduce the N,N-dimethylacrylamide (DMA) content in the formulation from 30% to 25% or lower, see Table 18.

Formulations having compositions shown in Table 18 were prepared in glass vials and mixed well to fully dissolve all components. The prepared formulations were then filtered through 0.2 μm syringe filters into fresh vials, degassed with nitrogen, and cast in air atmosphere into polypropylene slab molds or molds (net shaped 21D SN60WF and 40D SA60AT IOL lens wafers). Formulations were blue light cured at 55° C. for 1 hour.

TABLE 18

| | Concentration (parts by wt.) | | | | | |
|---|---|---|---|---|---|---|
| Component | 1 | 2 | 3 | 4 | 5 | 6 |
| PEA | 52.1 | 57.1 | 62.2 | 52.2 | 49.7 | 72.2 |
| DEGMBA | 15.0 | 10.0 | 5.0 | 20.0 | 20.0 | |
| DMAA | 30.0 | 30.0 | 30.0 | 25.0 | 27.5 | 25.0 |
| BDDA | 1.0 | 1.0 | 1.0 | 1.0 | 1.0 | 1.0 |
| oMTP | 1.8 | 1.8 | 1.8 | 1.8 | 1.8 | 1.8 |
| AL8739 | 0.04 | 0.04 | 0.04 | 0.04 | 0.04 | 0.04 |
| Irgacure 819 | 0.2 | 0.2 | 0.2 | 0.2 | 0.2 | 0.2 |
| Presence of RT → 35° C. latent haze | 5 to 8 hrs | 5 to 8 hrs | 5 to 8 hrs | none | 2 hrs | none |

Example 10

This example illustrates that a PEG-based hydrophilic agent can be used to ensure a more continuous distribution of water in the material during the transition through the latent haze limit and thereby allow the hydrated lens formulations to remain clear throughout the heating process from RT to 35° C. The preferred PEG-based monomer for the purpose of eliminating the latent haze phenomena was polyPEG, an alkylacrylate functionalized polymer of polyethylene glycol monomethylether methacrylate; and when used at a 3% concentration by weight, allows the IOL to remain clear throughout the latent haze transition.

Formulation: 74.2 wt. % of PEA; 20 wt. % of DMAA; 3.0 wt. % of polyethylene glycol methyl ether acrylate; 0.5 wt. % of BDDA; 0.5 wt. % HMBAA; 1.8 wt. % of oMTP; 0.04 wt. % of AL8739; and 0.2 wt. % of Irgacure 819.

The formulation was prepared in a glass vial and mixed well to fully dissolve all components. The prepared formulation was then filtered through 0.2 μm syringe filters into fresh vials, degassed with nitrogen, and cast in air atmosphere into polypropylene slab molds or molds (net shaped 21D SN60WF and 40D SA60AT IOL lens wafers). The formulation was blue light cured at 55° C. for 1 hour.

It is found that:
pre-extraction tackiness=43.8±4.2 N
BF MVs (per screen)=0 (autoclaved)
DF MVs (per screen)=100 (Autoclaved)
SLS (t=0, hydrated)=2.6±1.2 CCT
SLS (t=1 yr, hydrated)=12.1±3.5 CCT
SLS (t=5 yrs, hydrated)=15.0±8.9 CCT
SLS (t=10 yrs, hydrated)=13.9±2.3 CCT
Simulated 2.0 mm delivery, 40D/Monarch-III D=pass (no damage to lens/cartridge; good unfold)
Presence of RT→35° C. latent haze=none (pass)

Example 11

In the previous examples, N,N-dimethylacrylamide (DMAA) was used as the principal hydrophilic co-monomer for generating materials with low tack in the dry state, good foldability in the hydrated state, high refractive index, no microvacuoles, good optical clarity, and low surface scatter upon simulated accelerated aging. As an extension of this work, N-methylacrylamide (NMAA) was formulated in a similar manner as shown in Table 19 and the corresponding results are shown in Table 20. As expected, the equilibrium water content (EWC) values increased with higher NMAA loadings. Furthermore, the water contents of NMAA formulations were higher than the corresponding DMAA formulations due to the additional hydrogen bonding donor capabilities of NMAA. By contrast, DMAA is less hydrophilic since its nitrogen atom can only act as a hydrogen bond acceptor resulting in a lower water uptake. As shown in Table 20, formulations containing a minimum of 20% NMAA were obtained with good optical clarity, no microvacuoles, and acceptable tensile properties for delivery testing. All formulations showed low tack in the dry state.

TABLE 19

| | Concentration (parts by wt.) | | | | |
|---|---|---|---|---|---|
| Component | V | W | X | Y | Z |
| NMAA | 20.0 | 25.0 | 30.0 | 20.0 | 15.0 |
| PEA | 75.5 | 70.5 | 65.5 | 74.5 | 79.4 |
| BDDA | 2.7 | 2.7 | 2.7 | 3.7 | 3.8 |
| oMTP | 1.8 | 1.8 | 1.8 | 1.8 | 1.8 |
| AL8739 | 0.04 | 0.04 | 0.04 | 0.04 | 0.04 |
| AIBN | 1.0 | 1.0 | 1.0 | 1.0 | 1.0 |

TABLE 20

| | Corresponding Formulation | | | | |
|---|---|---|---|---|---|
| Properties | V | W | X | Y | Z |
| % Extractables | 3.2 | 3.7 | 3.8 | 3.3 | 3.1 |
| SD | 0.4 | 0.5 | 0.4 | 0.6 | 0.2 |
| BF MV | 0 | 0 | 0 | 0 | 5 |
| DF MV | <10 | <10 | <10 | <10 | >>10 |
| Clarity, | Clear | Clear | Clear | Clear | *Hazy |
| EWC, 35° C. | 5.0 | 7.3 | 10.2 | 5.1 | 3.2 |
| After MV test | 0.1 | 0.1 | 0.1 | 0.1 | 0.1 |
| Hydrated RI | 1.540 | 1.537 | 1.533 | 1.540 | 1.544 |
| Tensile Strength (MPa) | 4.67 ± 0.50 | 3.96 ± 0.38 | 2.56 ± 0.26 | 4.99 ± 0.33 | 5.36 ± 0.67 |
| Elongation at break (%) | 140 ± 6 | 136 ± 7 | 116 ± 5 | 126 ± 4 | 124 ± 7 |
| Young's Modulus (MPa) | 34.3 ± 3.3 | 27.7 ± 1.9 | 18.4 ± 3.0 | 31.3 ± 1.7 | 32.5 ± 1.8 |
| 25% Secant Modulus (MPa) | 3.19 ± 0.03 | 2.84 ± 0.06 | 2.35 ± 0.02 | 3.12 ± 0.03 | 3.93 ± 0.08 |
| 100% Secant Modulus (MPa) | 2.38 ± 0.02 | 2.19 ± 0.02 | 1.98 ± 0.02 | 3.23 ± 0.05 | 3.54 ± 0.06 |

*Formulation turned hazy after autoclaving and formed large microvacuoles

Example 12

N-hydroxyethyl acrylamide (HEAA) was subsequently used as the primary hydrophilic component. A formulation comprised of 30% HEAA and 66.7% PEA as the primary components resulted in phase separation of the monomers, with the higher density HEAA settling to the bottom. Reduction of HEAA to 20% resulted in a similar separation of the 2 monomers. A formulation comprised of 15% HEAA and 80% PEA resulted in better compatibility of the monomers but poorly cured test samples. To improve the solubility of HEAA in PEA, DMAA was added to better compatibilize the formulation and prevent phase separation. Representative examples are shown in Table 21. No phase separation of the monomer mixtures was observed and the resultant materials were clear upon curing and delta T microvacuole testing except for Formulation J shown in Table 22. As shown in Example A (Table 22), the use of 15% HEAA and 15% DMAA results in a material with a water content of approximately 9%, whereas formulations containing 30% DMAA have approximately half the water content. This signifies that HEAA is able to absorb more water than DMAA as a result of increased hydrogen bonding.

TABLE 21

| | Concentration (parts by wt.) | | | | | | | | | | |
|---|---|---|---|---|---|---|---|---|---|---|---|
| Component | A | B | C | D | E | F | G | H | I | J | K |
| HEAA | 15.0 | 15.0 | 15.0 | 10.0 | 10.0 | 7.50 | 7.50 | 10.0 | 10.0 | 5.00 | 12.0 |
| PEA | 66.7 | 65.2 | 65.2 | 65.7 | 65.7 | 80.2 | 80.2 | 75.2 | 75.2 | 70.2 | 70.7 |
| DMAA | 15.0 | 15.0 | 15.0 | 20.0 | 20.0 | 7.50 | 7.50 | 10.0 | 10.0 | 20.0 | 12.0 |
| BDDA | 1.5 | 3.0 | 3.0 | 2.5 | 2.5 | 3.0 | 3.0 | 3.0 | 3.0 | 3.0 | 3.5 |
| oMTP | 1.8 | 1.8 | 1.8 | 1.8 | 1.8 | 1.8 | 1.8 | 1.8 | 1.8 | 1.8 | 1.8 |
| AL8739 | 0.04 | 0.04 | 0.04 | 0.04 | 0.04 | 0.04 | 0.04 | 0.04 | 0.04 | 0.04 | 0.04 |
| AIBN | 0.5 | 0.5 | — | 0.5 | — | 0.5 | — | 0.5 | — | 0.5 | — |
| Perk | — | — | 1.8 | — | 1.8 | — | 1.8 | — | 1.8 | — | — |
| Luperox A98 | — | — | — | — | — | — | — | — | — | — | 1.0 |

TABLE 22

| Properties | A | B | C | D | E | F | G | H | I | J | K |
|---|---|---|---|---|---|---|---|---|---|---|---|
| % Extractables | 2.9 | 3.1 | 4.1 | 2.5 | 3.2 | 3.4 | 2.8 | 3.2 | 3.3 | 2.6 | 2.3 |
| SD | 0.6 | 0.9 | 2.1 | 0.6 | 0.2 | 0.7 | 0.2 | 0.7 | 0.4 | 0.6 | 0.1 |
| BF MV | 0 | 0 | 0 | 0 | 0 | 0 | 0 | 0 | 0 | 0 | 0 |
| DF MV | <10 | <10 | <10 | <10 | NT | >10 | >10 | >10 | >10 | NT | <10 |
| Clarity, | Clear | Clear | Clear | Clear | Clear | Clear | Clear | Clear | Clear | Hazy | Clear |
| EWC*, 35° C. | 8.9 | NT | NT | 7.9 | NT | 3.0 | NT | 4.6 | 4.7 | 5.0 | 6.0 |
| SD | 0.2 | | | 0.2 | | 0.1 | | 0.2 | 0.2 | 0.3 | 0.2 |
| Hydrated RI | 1.531 | 1.528 | 1.528 | 1.528 | NT | 1.542 | NT | 1.540 | 1.540 | 1.535 | 1.533 |
| Tensile Strength (MPa) | 2.0 ± 0.3 | 2.2 ± 0.2 | NT | 2.75 ± 0.31 | NT | 3.3 ± 0.4 | NT | 3.4 ± 0.4 | NT | NT | 2.3 ± .5 |
| Elongation at break (%) | 130 ± 8 | 90 ± 4 | NT | 113 ± 7 | NT | 115 ± 5 | NT | 117 ± 7 | NT | NT | 83 ± 12 |
| Young's Modulus(MPa) | 17.1 ± 3.9 | 16.5 ± 3.5 | NT | 18.4 ± 2.7 | NT | 21.6 ± 2.9 | NT | 21.8 ± 2.5 | NT | NT | 19.2 ± 2.8 |
| 100% Secant Modulus (MPa) | 1.24 ± 0.01 | 2.43 ± 0.05 | NT | 2.18 ± 0.04 | NT | 2.46 ± 0.05 | NT | 2.47 ± 0.11 | NT | NT | NM |

NT = not tested;
NM = not measured;
*After MV test

Example 13

Polyacrylamide has a reported Tg of 165° C., which is considerably higher than that of poly(N,N-dimethylacrylamide) (Tg=89° C.), so acrylamide (AA) was targeted for lowering tack. Similar to DMAA, NMAA, and HEAA, formulations containing acrylamide (AA) and PEA were prepared to give materials with sufficiently low tack in the dry state and a high degree of softness in the hydrated state due to water absorption as a result of hydrogen bonding via AA. Initial formulations comprised of 10-20% AA and 75-85% PEA as co-monomers were incompatible. AA is a crystalline solid (melting point=84.5° C.) which is insoluble in aromatic acrylic monomers such as PEA at ambient temperature. Heating of the monomer mixture to 60-80° C. improved the solubility, but AA immediately precipitated out upon cooling to ambient temperature. As previously observed with HEAA, DMAA was used as a compatibilizer to help maintain a homogeneous mixture throughout the casting and curing process. PEA and AA-containing formulations were prepared as shown in Table 23 and the corresponding data are shown in Table 24. Formulations were clear and showed good optical clarity, but the materials were more prone to microvacuole formation and generally stiffer than corresponding formulations containing DMAA, NMAA, and HEAA.

TABLE 23

| | Concentration (parts by wt.) | | | | |
|---|---|---|---|---|---|
| Component | A | B | C | D | E |
| AA | 10.1 | 5.01 | 8.00 | 5.00 | 6.67 |
| PEA | 65.1 | 75.6 | 75.6 | 75.6 | 75.2 |
| DMAA | 20.0 | 15.0 | 12.0 | 15.0 | 13.3 |
| BDDA | 3.0 | 2.5 | 2.5 | 2.6 | 3.0 |
| oMTP | 1.8 | 1.8 | 1.8 | 1.8 | 1.8 |
| AL8739 | 0.04 | 0.04 | 0.04 | 0.04 | 0.04 |
| AIBN | 0.5 | — | — | 0.5 | 0.5 |
| Irgacure 819 | — | 0.3 | 0.3 | — | — |

TABLE 24

| | Corresponding Formulation | | | | |
|---|---|---|---|---|---|
| Properties | A | B | C | D | E |
| % Extractables | 3.1 | 1.2 | 1.3 | 2.3 | 2.3 |
| SD | 0.7 | 0.1 | 0.1 | 0.6 | 0.4 |
| BF MV | 0 | 5 | 3 | 5 | 0 |
| DF MV | <10 | >10 | >10 | >10 | <10 |
| Clarity, | Clear | Clear | Clear | Clear | Clear |
| EWC*, 35° C. | 8.4 | 3.8 | 4.6 | 3.8 | 4.3 |
| SD | 0.2 | 0.2 | 0.1 | 0.1 | 0.1 |
| Hydrated RI | 1.532 | 1.542 | 1.542 | 1.540 | 1.540 |
| Tensile Strength (MPa) | NT | 5.4 ± 0.3 | 5.6 ± 0.4 | 7.5 ± 0.8 | 9.7 ± 0.9 |
| Elongation at break (%) | NT | 160 ± 5 | 165 ± 5 | 173 ± 8 | 159 ± 8 |
| Young's Modulus (MPa) | NT | 44.9 ± 3.4 | 54.4 ± 3.4 | 89.1 ± 4.5 | 117 ± 11 |
| 25% Secant Modulus (MPa) | NT | 3.68 ± 0.07 | 4.22 ± 0.07 | 5.59 ± 0.22 | 8.24 ± 0.34 |
| 100% Secant Modulus (MPa) | NT | 2.43 ± 0.05 | 2.48 ± 0.03 | 3.11 ± 0.08 | 4.76 ± 0.12 |

NT = not tested

We claim:

1. A polymeric ophthalmic device material, having: (1) a glass transition temperature of from about 28° C. to about 40° C. in a dry state; (2) a glass transition temperature of about 20° C. or lower in a fully hydrated state; (3) a refractive index of greater than 1.50 measured at 589 nm and at 23±3° C. in the fully hydrated state; (4) an equilibrium water content of from about 5% to 11% by weight at a temperature of from 16° C. to 45° C.; (5) a glistening resistance characterized by having no bright field microvacuole and about 10 or less microvacuoles per viewing screen in glistering tests; (5) a Young's modulus of from about 5.0 MPa to 35.0 MPa; and (6) a 100% secant modulus of less than 5.0 MPa, wherein the ophthalmic device material is a polymerization product of a polymerizable composition selected from the group consisting of composition A1, composition A2, and composition A3, wherein composition A1 comprises (a1) from about 18% to about 32% by weight of N,N-dimethylacrylamide, (b1) at least one hydrophobic acrylamido component selected from the group consisting of N-butyl acrylamide, N-butoxymethyl acrylamide, and N-methoxypropyl acrylamide, (c1) from about 40% to about 76% by weight of said one or more aryl acrylic monomers of formula (I)

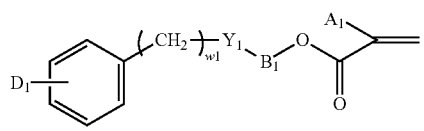

(I)

wherein $A_1$ is H or $CH_3$; $B_1$ is $(CH_2)_{m1}$ or $[O(CH_2)_2]_{z1}$ in which m1 is 2-6 and z1 is 1-10; $Y_1$ is a direct bond, O, S, or NR' in which R' is H, $CH_3$, $C_{n'}H_{2n'+1}$ in which n'=1-10, iso-$OC_3H_7$, $C_6H_5$, or $CH_2C_6H_5$; W1 is 0-6, provided that m1+w1≤8; and $D_1$ is H, Cl, Br, $C_1$-$C_4$ alkyl, $C_1$-$C_4$ alkoxy, $C_6H_5$, or $CH_2C_6H_5$, (d1) from about 0.4% to about 2.5% by weight of at least one first polymerizable crosslinking agent, wherein composition A2 comprises (a2) from about 15% to about 35% by weight of N-methylacrylamide, (b2) from about 0.4% to about 2.5% by weight of at least one second polymerizable crosslinking agent, (c2) from about 60% to about 80% by weight of one or more aryl acrylic monomers of formula (I) as defined above, wherein composition A3 comprises (a3) from about 10% to about 35% by weight of a mixture of N,N-dimethylacrylamide and N-hydroxyethylacrylamide, (b3) from about 0.4% to about 2.5% by weight of at least one third polymerizable crosslinking agent, (c3) from about 60% to about 80% by weight of one or more aryl acrylic monomers of formula (I) as defined above, wherein the first, second, and third polymerizable crosslinking agents are selected from the group consisting of ethylene glycol dimethacrylate, diethylene glycol dimethacrylate, triethylene glycol dimethacrylate, tetraethylene glycol dimethacrylate, allyl methacrylate, 1,3-propanediol dimethacrylate, 2,3-propanediol dimethacrylate, 1,6-hexanediol dimethacrylate, 1,4-butanediol dimethacrylate, ethylene glycol diacrylate, diethylene glycol diacrylate, triethylene glycol diacrylate, tetraethylene glycol diacrylate, allyl acrylate, 1,3-propanediol diacrylate, 2,3-propanediol diacrylate, 1,6-hexanediol diacrylate, 1,4-butanediol diacrylate, N,N'-hexamethylene bismethacrylamide, N,N'-dihydroxyethylene bisacrylamide, N,N'-dihydroxyethylene bismethacrylamide, N,N'-methylene bisacrylamide, and N,N'-methylene bismethacrylamide.

2. The ophthalmic device material of claim 1, wherein the device material in the fully hydrated state has an elongation at break of greater than 90%.

3. The ophthalmic device material of claim 2, wherein the device material in the fully hydrated state has a surface light scattering of about 30 CCT or less after 10-years accelerated aging (90° C., 81 days in a balanced salt solution).

4. The ophthalmic device material of claim 3, wherein the device material in the fully hydrated state remains substantially clear when being heated from 23° C. to 35° C.

5. The ophthalmic device material of claim 4, wherein in formula (I), $B_1$ is $(CH_2)_{m1}$, m1 is 2-5, $Y_1$ is nothing or O, w1 is 0 or 1, and $D_1$ is H.

6. The ophthalmic device material of claim 4, wherein said one or more aryl acrylic monomers of formula (I) are: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl)ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl)ethyl acrylate; 2-(4-cyclohexylphenyl)ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.

7. The ophthalmic device material of claim 4, wherein said one or more aryl acrylic monomers are: 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; 2-[2-(benzyloxy)ethoxy]ethyl acrylate; or combinations thereof.

8. The ophthalmic device material of claim 7, wherein the polymerizable composition is composition A1.

9. The ophthalmic device material of claim 8, wherein the polymerizable composition further comprises at least one component selected from the group consisting of:
(i) from about 5% to about 15% by weight of hydroxyethyl methacrylate;
(ii) from about 1% to about 5% by weight of a poly(ethylene glycol)-containing polymerizable component of formula (II),

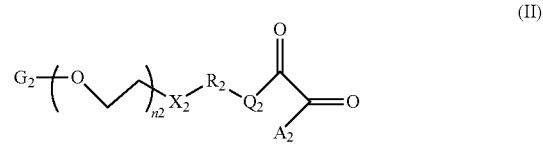

(II)

wherein: $A_2$ is H or $CH_3$; $Q_2$ and $Q_2'$ independent of each other are a direct bond, O, NH, or C(=O)NHCH$_2$CH$_2$O; $X_2$ and $X_2'$ independent of each other are a direct bond, O, NH, OC(=O)NH, or NHC(=O)NH; $R_2$ and $R_2'$ independent of each other are a direct bond, or $(CH_2)_p$; $p$=1-3; $G_2$ is H, $C_1$-$C_4$ alkyl, $(CH_2)_{m2}NH_2$, $(CH_2)_{m2}CO_2H$, or $R_2'$—$X_2'$-$Q_2'$-C(=O)CA$_2$=CH$_2$; m2=2-6; and n2=45-225 when G=H, $C_1$-$C_4$ alkyl, $(CH_2)_{m2}NH_2$, or $(CH_2)_{m2}CO_2H$; otherwise, n2=51-225;

(iii) a polymerizable UV-absorbing agent; and
(iv) a combination thereof.

10. The ophthalmic device material of claim 9, wherein the poly(ethylene glycol)-containing polymerizable component of formula (II) has a number average molecular weight of 2,000-10,000 Daltons.

11. The ophthalmic device material of claim 7, wherein the polymerizable composition is composition A2.

12. The ophthalmic device material of claim 11, wherein the polymerizable composition further comprises at least one component selected from the group consisting of:
(i) from about 5% to about 15% by weight of hydroxyethyl methacrylate;
(ii) from about 1% to about 5% by weight of a poly(ethylene glycol)-containing polymerizable component of formula (II),

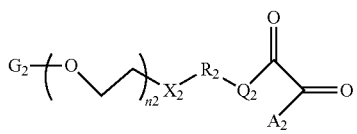

(II)

wherein: $A_2$ is H or $CH_3$; $Q_2$ and $Q_2'$ independent of each other are a direct bond, O, NH, or C(=O)NHCH$_2$CH$_2$O; $X_2$ and $X_2'$ independent of each other are a direct bond, O, NH, OC(=O)NH, or NHC(=O)NH; $R_2$ and $R_2'$ independent of each other are a direct bond, or $(CH_2)_p$; $p$=1-3; $G_2$ is H, $C_1$-$C_4$ alkyl, $(CH_2)_{m2}NH_2$, $(CH_2)_{m2}CO_2H$, or $R_2'$—$X_2'$-$Q_2'$-C(=O)CA$_2$=CH$_2$; m2=2-6; and n2=45-225 when G=H, $C_1$-$C_4$ alkyl, $(CH_2)_{m2}NH_2$, or $(CH_2)_{m2}CO_2H$; otherwise, n2=51-225;

(iii) a polymerizable UV-absorbing agent; and
(iv) a combination thereof.

13. The ophthalmic device material of claim 12, wherein the poly(ethylene glycol)-containing polymerizable component of formula (II) has a number average molecular weight of 2,000-10,000 Daltons.

14. The ophthalmic device material of claim 7, wherein the polymerizable composition is composition A3.

15. The ophthalmic device material of claim 14, wherein the polymerizable composition further comprises at least one component selected from the group consisting of:
(i) from about 5% to about 15% by weight of hydroxyethyl methacrylate;
(ii) from about 1% to about 5% by weight of a poly(ethylene glycol)-containing polymerizable component of formula (II),

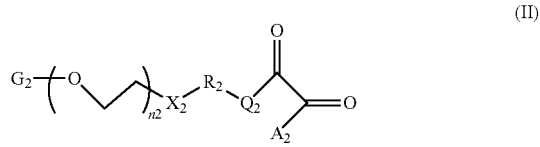

(II)

wherein: $A_2$ is H or $CH_3$; $Q_2$ and $Q_2'$ independent of each other are a direct bond, O, NH, or C(=O)NHCH$_2$CH$_2$O; $X_2$ and $X_2'$ independent of each other are a direct bond, O, NH, OC(=O)NH, or NHC(=O)NH; $R_2$ and $R_2'$ independent of each other are a direct bond, or $(CH_2)_p$; $p$=1-3; $G_2$ is H, $C_1$-$C_4$ alkyl, $(CH_2)_{m2}NH_2$, $(CH_2)_{m2}CO_2H$, or $R_2'$—$X_2'$-$Q_2'$-C(=O)CA$_2$=CH$_2$; m2=2-6; and n2=45-225 when G=H, $C_1$-$C_4$ alkyl, $(CH_2)_{m2}NH_2$, or $(CH_2)_{m2}CO_2H$; otherwise, n2=51-225;

(iii) a polymerizable UV-absorbing agent; and
(iv) a combination thereof.

16. The ophthalmic device material of claim 15, wherein the poly(ethylene glycol)-containing polymerizable component of formula (II) has a number average molecular weight of 2,000-10,000 Daltons.

17. The ophthalmic device material of claim 1, wherein the polymerizable composition comprises 1,6-hexanediol diacrylate, 1,4-butanediol diacrylate, or a combination thereof.

18. The ophthalmic device material of claim 4, wherein the polymerizable composition comprises a 1,6-hexanediol diacrylate, 1,4-butanediol diacrylate, or a combination thereof.

19. The ophthalmic device material of claim 7, wherein the polymerizable composition comprises 1,6-hexanediol diacrylate, 1,4-butanediol diacrylate, or a combination thereof.

20. An intraocular lens comprising an ophthalmic device material of claim 1.

* * * * *